US007060291B1

(12) United States Patent
Meers et al.

(10) Patent No.: US 7,060,291 B1
(45) Date of Patent: Jun. 13, 2006

(54) MODULAR TARGETED LIPOSOMAL DELIVERY SYSTEM

(75) Inventors: Paul R. Meers, Princeton Junction, NJ (US); Tong Shangguan, Princeton, NJ (US); Donna Cabral-Lilly, Princeton, NJ (US); Patrick Ahl, Princeton, NJ (US); Ravi Erukulla, Plainsboro, NJ (US); Andrew Janoff, Princeton Junction, NJ (US)

(73) Assignee: Transave, Inc., Monmouth Junction, NJ (US)

( * ) Notice: Subject to any disclaimer, the term of this patent is extended or adjusted under 35 U.S.C. 154(b) by 78 days.

(21) Appl. No.: 10/130,951

(22) PCT Filed: Nov. 17, 2000

(86) PCT No.: PCT/US00/31712

§ 371 (c)(1),
(2), (4) Date: May 24, 2002

(87) PCT Pub. No.: WO01/37807

PCT Pub. Date: May 31, 2001

Related U.S. Application Data

(60) Provisional application No. 60/167,297, filed on Nov. 24, 1999, provisional application No. 60/209,088, filed on Jun. 2, 2000.

(51) Int. Cl.
*A61K 9/127* (2006.01)

(52) U.S. Cl. .................. 424/450; 424/1.21; 424/9.321; 424/9.51; 424/417

(58) Field of Classification Search ................ 424/450, 424/1.21, 9.321, 9.51, 417
See application file for complete search history.

(56) References Cited

U.S. PATENT DOCUMENTS

| 5,534,259 A | * | 7/1996 | Zalipsky et al. ............ 424/450 |
| 5,935,599 A | | 8/1999 | Dadey |
| 6,287,857 B1 | * | 9/2001 | O'Riordan et al. ...... 435/320.1 |

OTHER PUBLICATIONS

Huang, A. et al., "Monoclonal Antibody Covalenty Coupled With Fatty Acid", The Journal of Biological Chemistry, Sep. 10, vol. 255, No. 17, pp. 8015-8018.

* cited by examiner

*Primary Examiner*—Gollamudi S. Kishore
(74) *Attorney, Agent, or Firm*—Foley Hoag LLP

(57) ABSTRACT

A liposome including a fusogenic liposome, a linking moiety and a targeting moiety. The fusogenic liposome is a lipid bilayer encapsulating contents. The linking moiety is electrostatically bound to the lipid bilayer, and the targeting moiety is covalently bound to the linking moiety. The liposome may also include a stabilizing moiety interposed between the linking and targeting moieties, and covalently bound to both. Alternatively, the stabilizing and targeting moieties may be covalently bound to separate linking moieties, the linking moieties being electrostatically bound to the lipid bilayer.

10 Claims, 21 Drawing Sheets

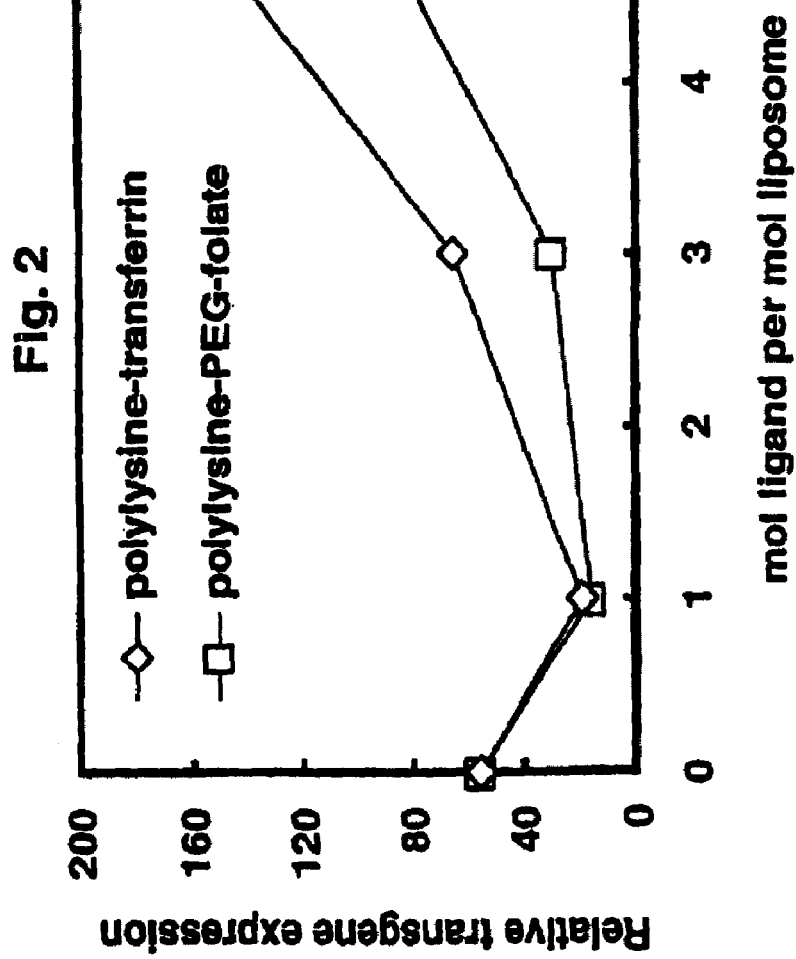

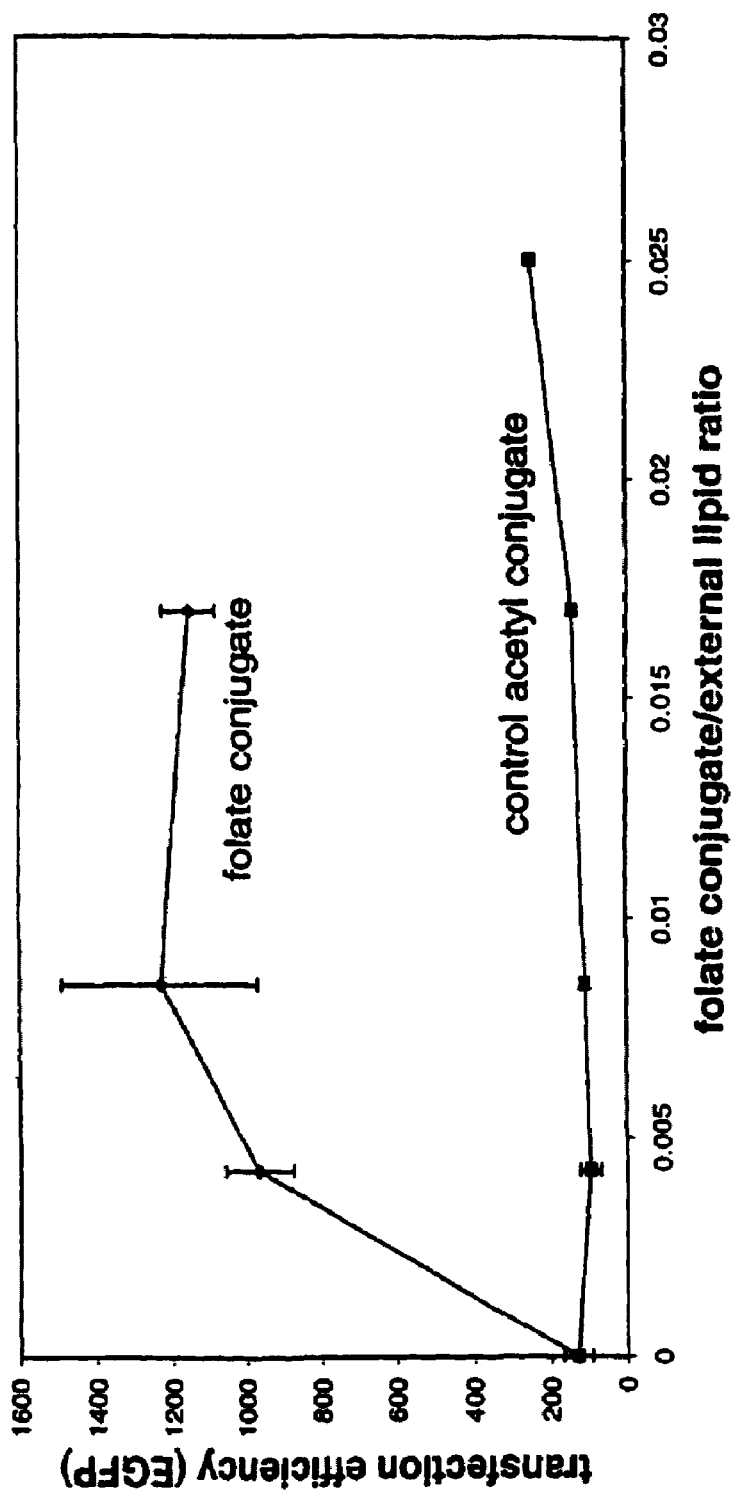

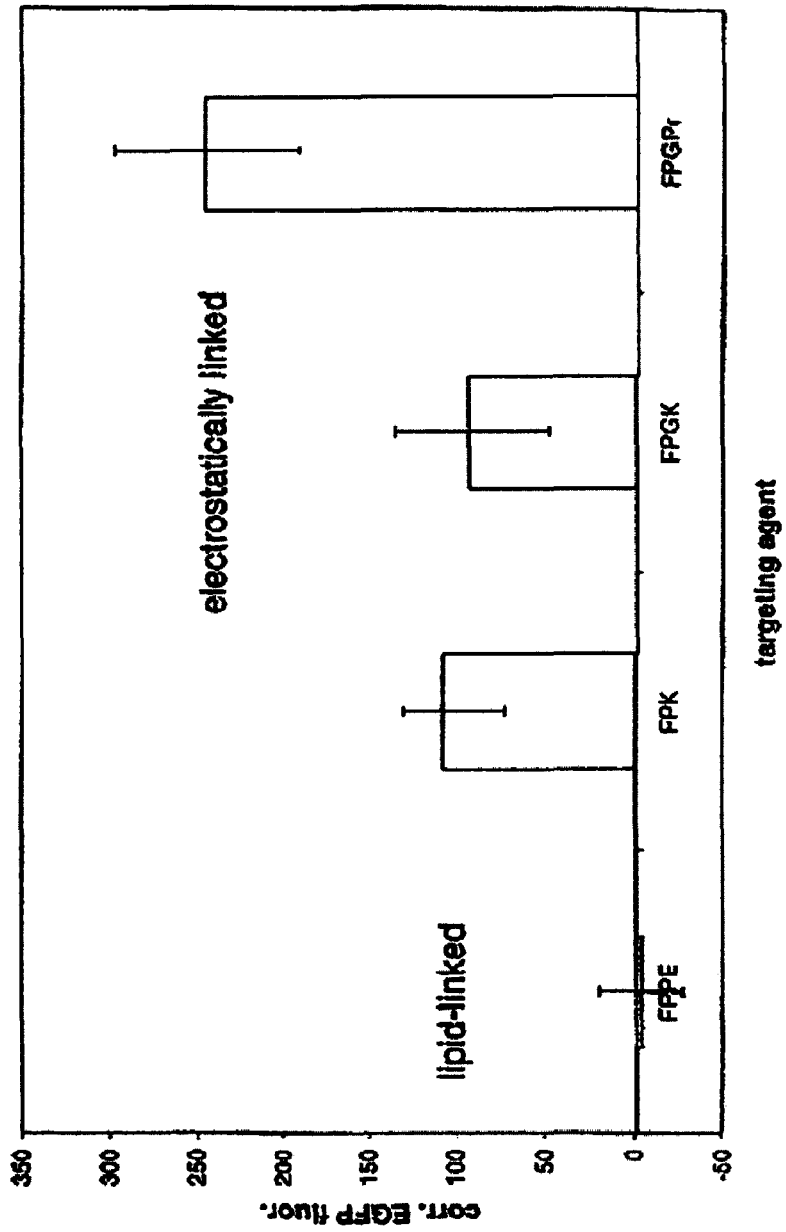

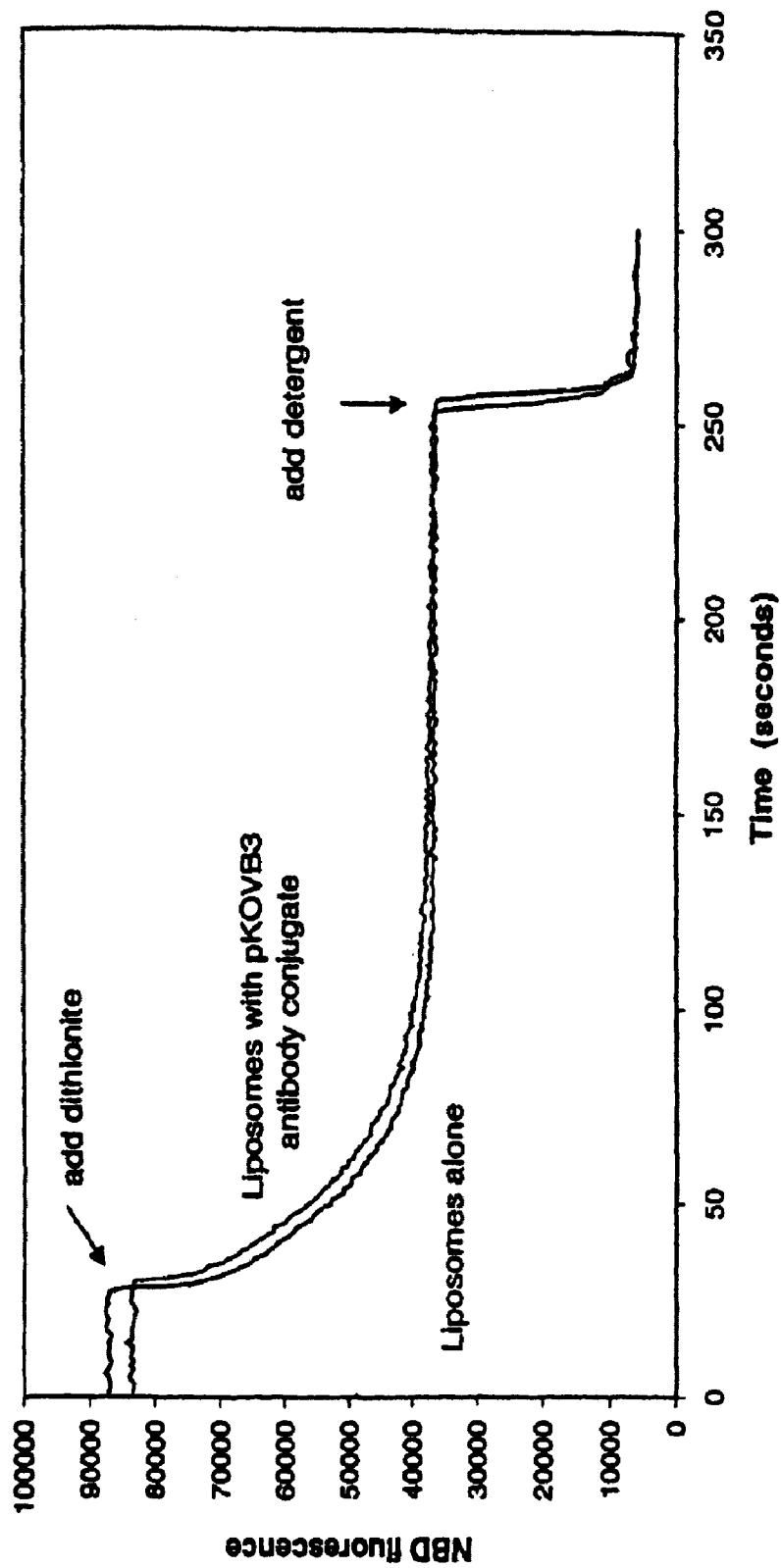

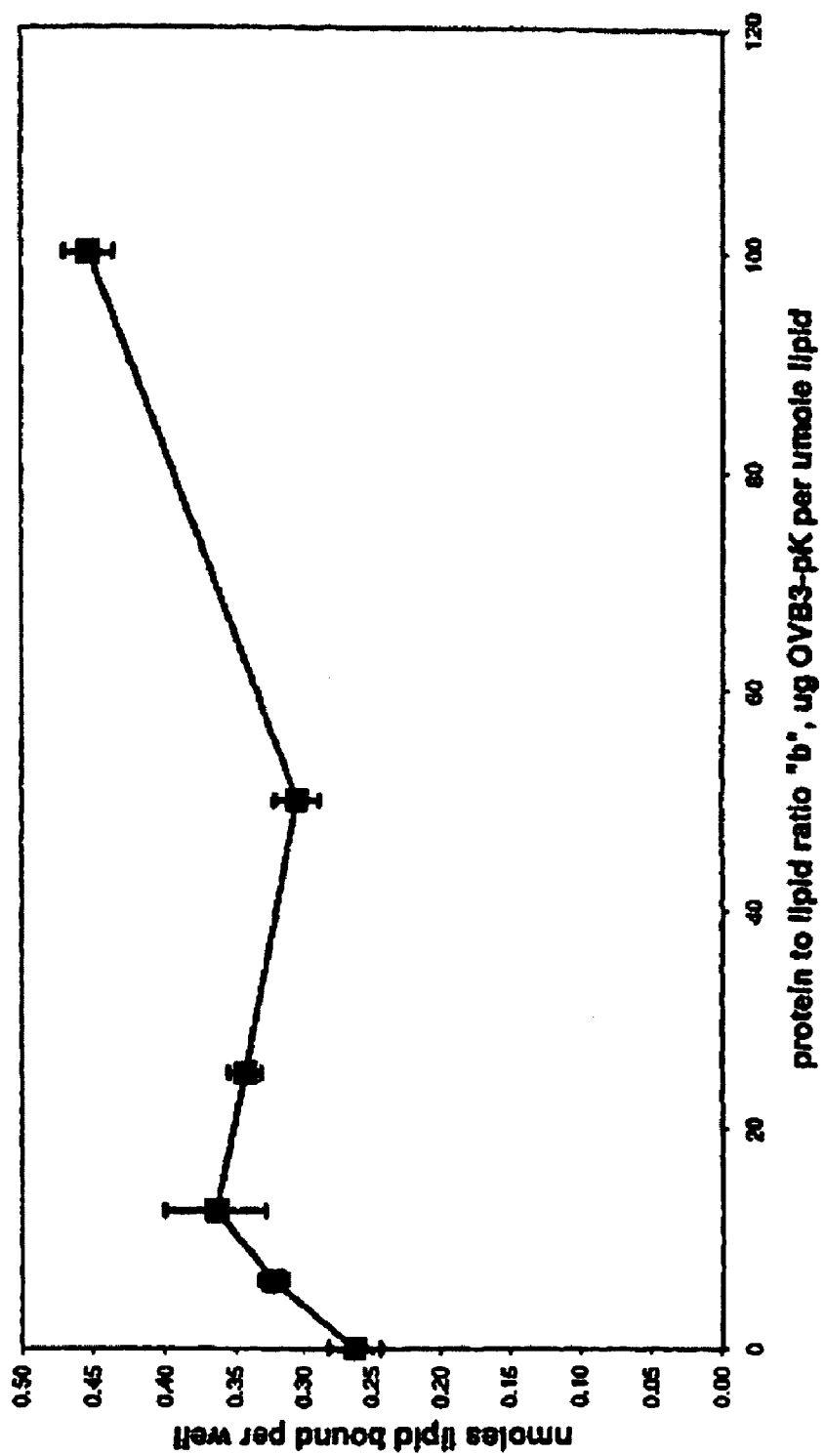

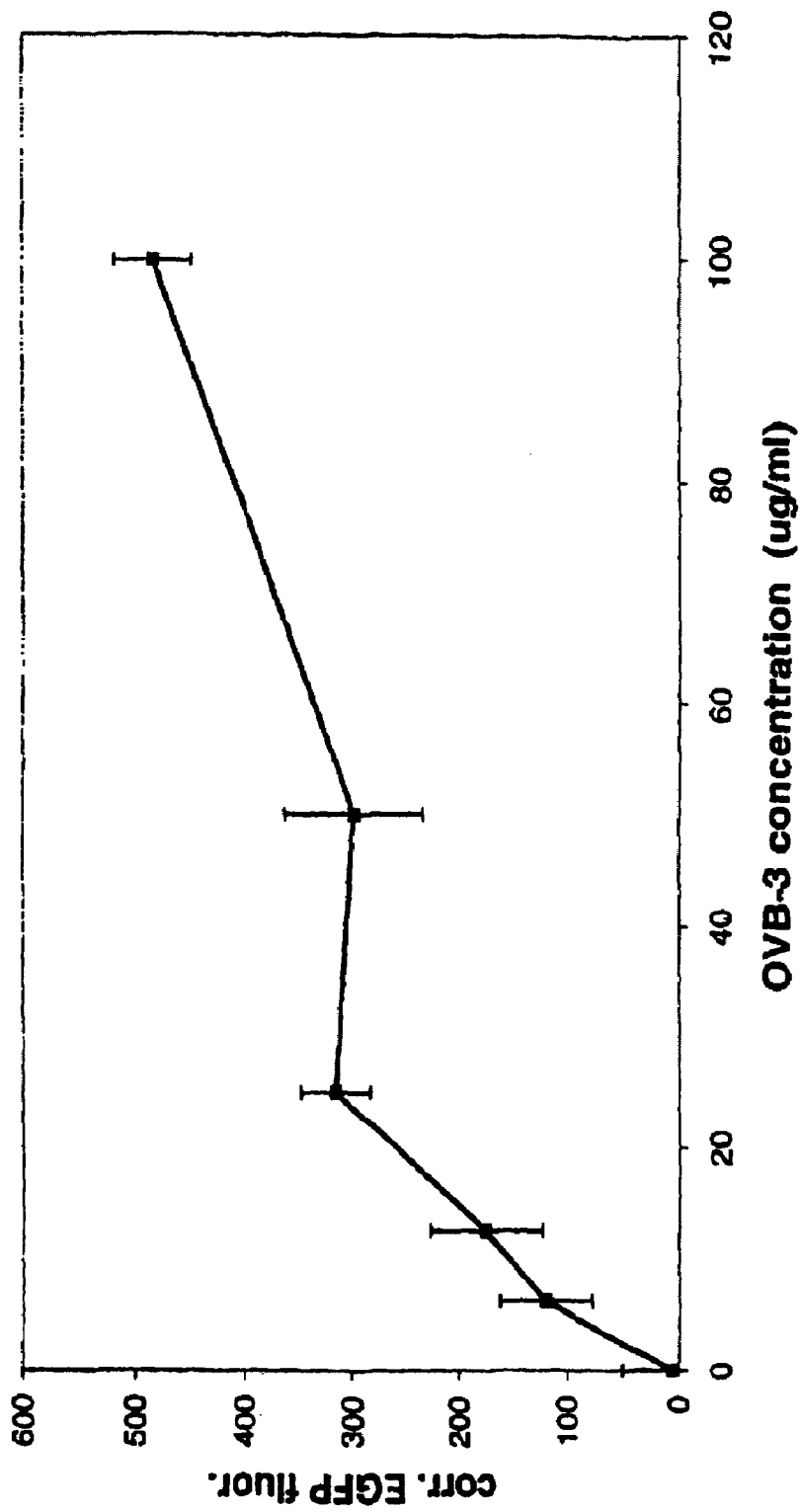

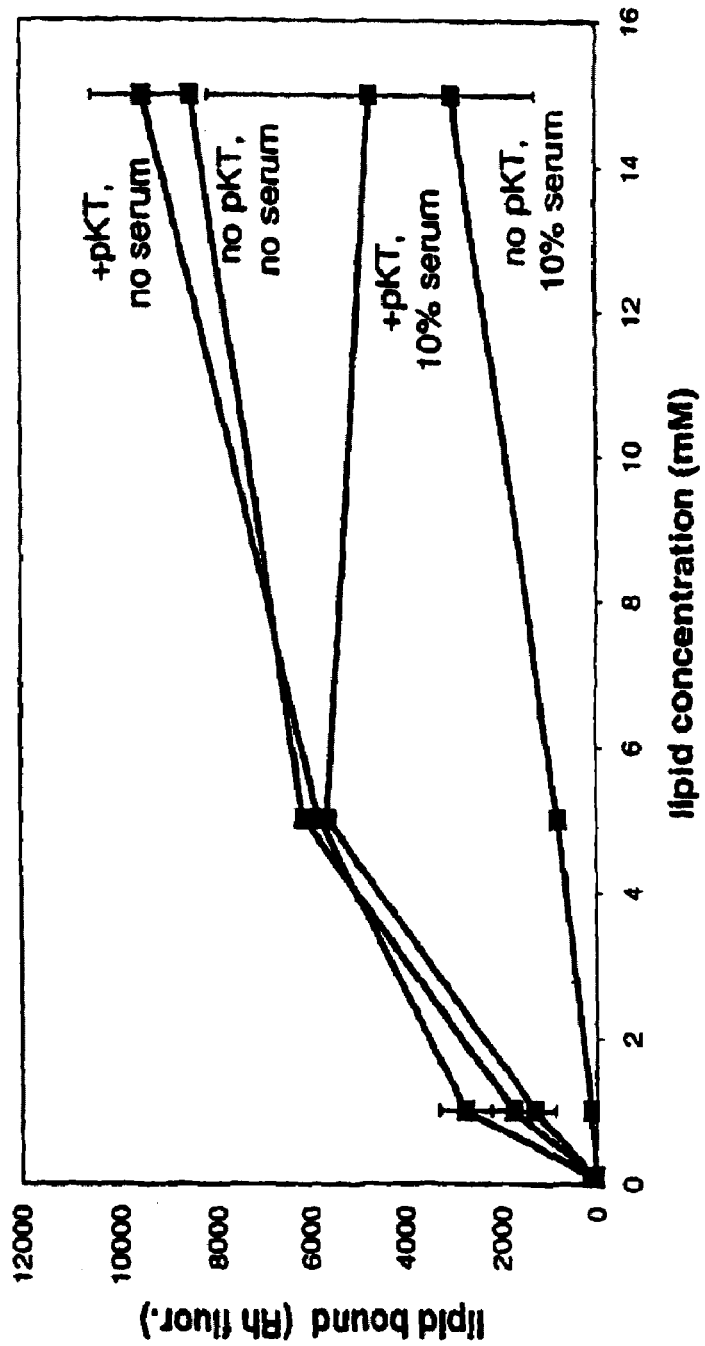
Fig. 9: Binding of liposomes to OVCAR-3 cells; effect of pKT

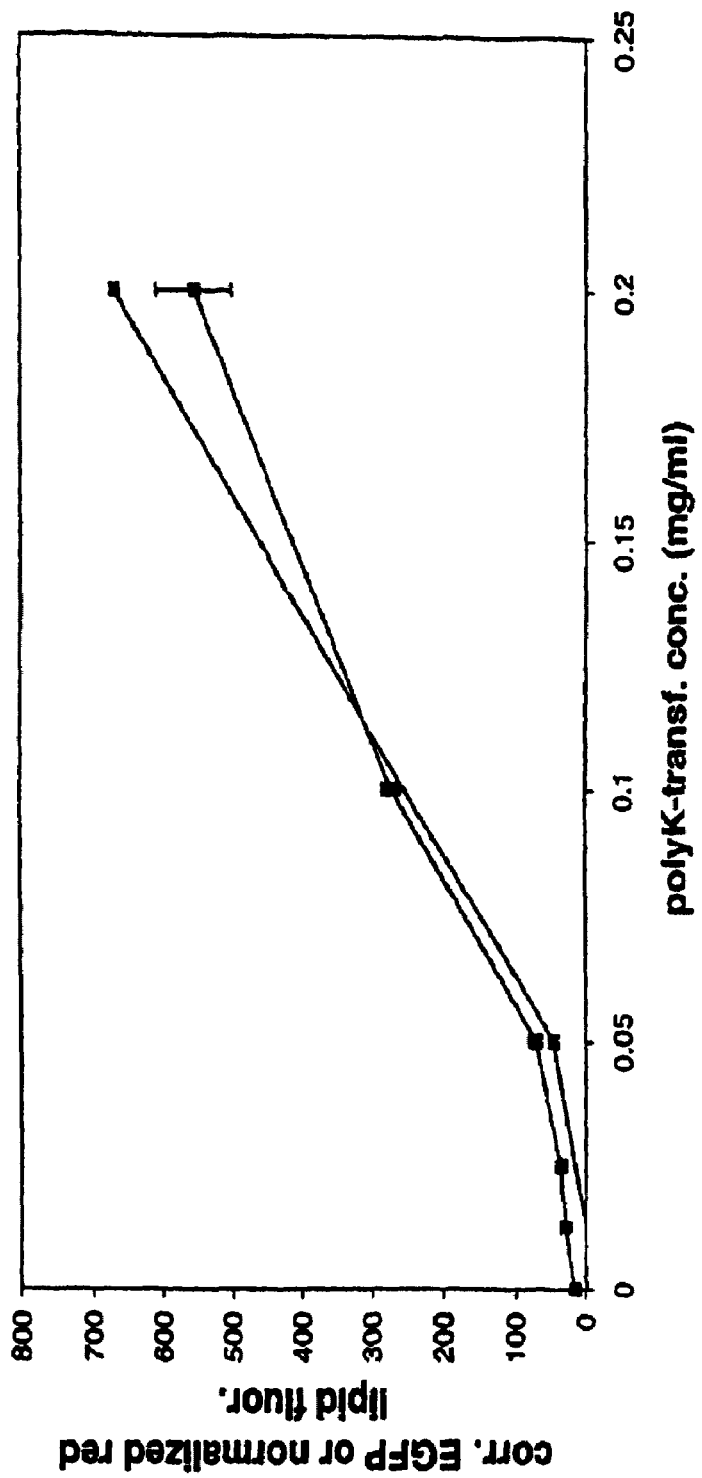

Non-specific IgG

Anti-Transferrin

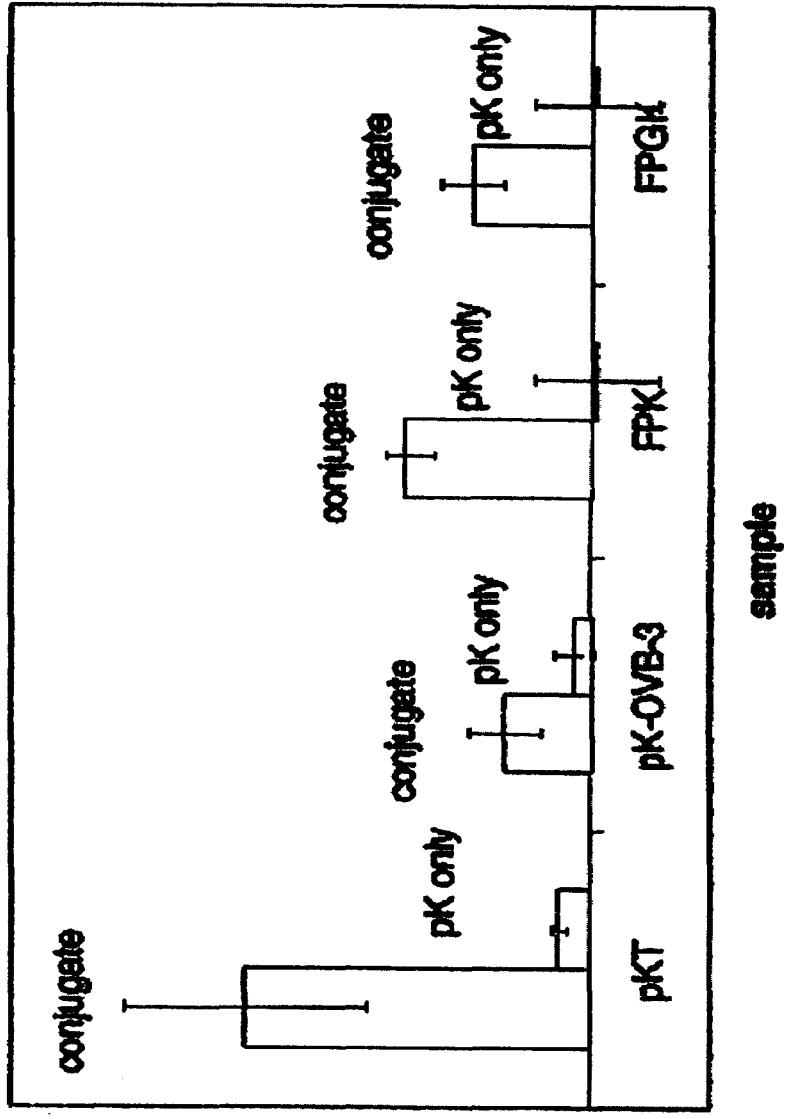

Without polylysine-transferrin

Without polylysine-transferrin

Fig 14C
With polylysine-transferrin
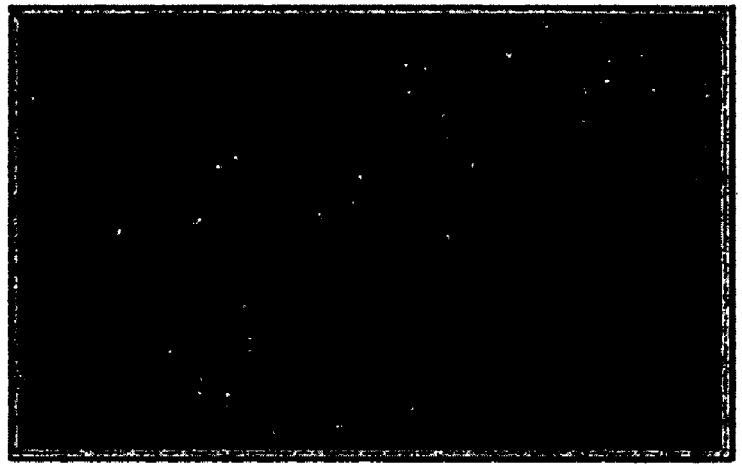
14D
With polylysine-transferrin

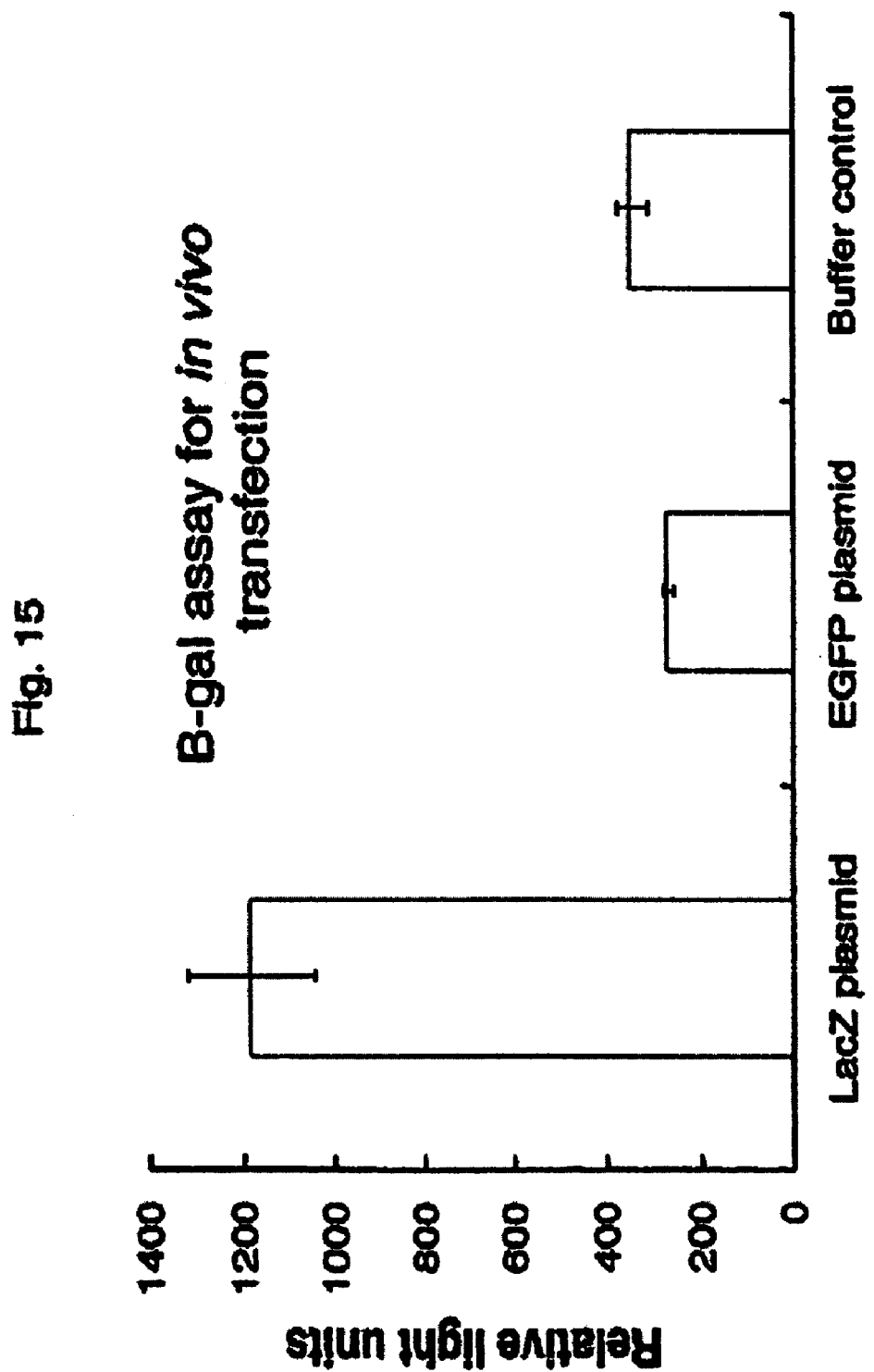

MODULAR TARGETED LIPOSOMAL DELIVERY SYSTEM

FIELD OF THE INVENTION

The invention relates to a targeted liposome capable of efficient intracellular delivery of one or more bioactive agents, a pharmaceutical composition including the targeted liposome, and a method of delivering the contents of a liposome to an in vivo or in vitro target site such as a tumor cell, site of inflammation or infection.

BACKGROUND OF THE INVENTION

Pharmaceutical usefulness of bioactive agents depends upon the ability to position therapeutically-effective quantities of intact agent at the target site in the patient. Delivering intact bioactive agents to target sites can be difficult: In vivo degradation of bioactive agents can occur, as well as absorption/retention of the agent by non-targeted systems. Even if pharmaceutically effective amounts of intact agent can be delivered to the vicinity of the target site, accessing the functional location of the site for the bioactive agent can be challenging, particularly if that location is intracellular. For example, certain polar compounds and many large molecules can not enter cells at all because of their inability to cross target cell membranes. In addition, dilution of the bioactive agent by non-specific binding to non-target sites reduces the amount of bioactive agent available to the target site.

Yet another challenge in the therapeutic delivery of drugs or bioactive agents is limiting the toxicities often associated with therapeutically effective concentrations of drugs or bioactive agents. Delivery to a specific target site can also reduce some toxicity normally associated with the administration of a drug or agent. Even when a drug or bioactive agent has no toxicity associated with it, the "loss" of agent through degradation, removal by non-target organs and other delivery failures can significantly and prohibitively increase the cost of the therapy or decrease the efficacy.

One method used to deliver bioactive agents or drugs to tissues and cells is to encapsulate the bioactive agents or drugs in liposomes. Often, an added advantage to this type of formulation is the reduction of the toxicity associated with certain drugs or bioactive agents. The intracellular targeting possibilities that liposomes provide are especially intriguing. While certain cells are known to engulf liposomes, delivery of most liposomes to a target site is not sufficient to deliver the encapsulated contents to the interior of the cell. Fusogenic liposomes are known that allow the liposome's bilayer to fuse with the cell membrane and thus, deliver the encapsulated bioactive agents or drugs to the cell. However, often these fusogenic liposomes lack stability when incubated in serum. In addition, most fusogenic liposomes have not heretofore been able to be targeted to the specific site where the bioactive agent or drug is required. Efficient liposomal delivery to cells in vivo requires specific targeting and substantial protection from the extracellular environment, particularly serum proteins. Unfortunately, most known targeting and protecting strategies also generate large steric barriers on the surface of the liposomes that limit or prohibit fusogenic delivery of the liposomal contents into the interior of the cell. In addition, known targeting and protecting strategies attach targeting/protecting molecules to the liposome through hydrophobic bonding to the liposome's lipid bilayer. These hydrophobic bonds usually inhibit the function of fusogenic membranes. When the hydrophobic moiety is designed to allow dissociation of the targeting/protecting moiety, its dissociation does not occur specifically at the target site.

SUMMARY OF THE INVENTION

Briefly, the invention is a modular liposomal targeting and delivery system comprising a fusogenic liposome, a linking moiety and a targeting moiety. In an alternate embodiment, the system may comprise a stabilizing moiety, either instead of or in addition to the targeting moiety. The fusogenic liposome comprises a lipid bilayer encapsulating contents to be delivered to a target site such as a tumor, a site of inflammation or infection and/or to the cytoplasm of a cell. The liposomes may contain one or more bioactive agents or drugs or may contain a combination of bioactive agents and drugs. In one embodiment, the bioactive agent is a nucleic acid, preferably DNA. The targeting and/or the stabilizing moiety is covalently bound to one or more linking moieties, and the linking moiety electrostatically binds at neutral pH to the lipid bilayer of the fusogenic liposome. The linking moiety is selected from the group consisting of polylysine, protamine, polyethyleneimine, polyarginine, polyacrylate, a spermine derivative, cytochrome c, an annexin, heparin sulfate, an aminodextran, polyaspartate, polyglutamate, a polysialic acid, and/or poly(2-ethylacrylic acid). The targeting moiety is a molecule that will bind selectively to the surface of targeted cells. For instance, the targeting molecule may be a ligand that binds to the cell surface receptor found on a particular cell type or expressed at a higher frequency on target cells than on other cells. The targeting moiety is selected from the group consisting of a vitamin, transferrin, an antibody or fragment thereof, sialyl Lewis X antigen, hyaluronic acid, mannose derivatives, glucose derivatives, cell specific lectins, galaptin, galectin, lactosylceramide, a steroid derivative, an RGD sequence, EGF, EGF-binding peptide, urokinase receptor binding peptide, a thrombospondin-derived peptide, an albumin derivative and/or a molecule derived from combinatorial chemistry. The targeting moiety enhances the ability of the liposome to bind to a targeted cell and to deliver the liposomal contents to the target site. While not being limited to the following explanation of the mechanism by which the present invention delivers the liposomal contents to the cellular interior, it has been theorized that after the liposome binds to a cell, an endocytosis pathway may be provoked, wherein the liposome is engulfed and sequestered in an endosomal compartment within the cell. The low pH (relative to the extracellular plasma) within the endosomal compartment weakens the electrostatic bond between the linking moiety and the liposome, wherein at least a portion of the linking moiety (and targeting moiety covalently bound thereto) dissociates at least temporarily from the liposome to expose the fusogenic lipid bilayer and enable fusion of the liposomal membrane and endosomal membrane. Release of the liposomal contents into the cytoplasm of the cell results from the fusion. Even if the endocytosis pathway is not initiated when the liposome binds to the cell, a low pH immediately surrounding the cell (relative to the plasma pH beyond the immediate vicinity of the cell) could cause at least temporary dissociation of the linking moiety from the liposome as described above, thereby enabling release of the liposomal contents into the cell cytoplasm.

Preferably, the invention also comprises a stabilizing moiety that is indirectly attached to the lipid bilayer of the fusogenic liposome through a linking moiety. The stabilizing moiety is covalently bound to the linking moiety, which linking moiety is electrostatically bound or can be electrostatically bound to the lipid bilayer at or near neutral pH, i.e., the pH of normal serum. A targeting moiety may also be covalently bound to the stabilizing moiety. Preferably, the stabilizing moiety is selected from the group consisting of polyethylene glycol, polyvinylpyrolidone, a dextran, a polyamino acid, methyl-polyoxazoline, polyglycerol, poly (acryloyl morpholine), and/or polyacrylamide.

In one embodiment, the invention is a composition comprising a fusogenic liposome comprising a lipid bilayer encapsulating contents; and a linking moiety electrostatically bound to said lipid bilayer; wherein a targeting moiety is covalently bound to said linking moiety.

The invention also encompasses a method of introducing a bioactive agent into a cell, comprising preparing a fusogenic liposome having a lipid bilayer which encapsulates a bioactive agent, electrostatically linking a targeting moiety to said fusogenic liposome to form a targeted liposome, contacting the targeted liposome with a cell such that the targeting moiety is released from at least a portion of the lipid bilayer of the liposome to expose a portion of the lipid bilayer, and fusing the exposed lipid bilayer portion with a cell membrane such that the bioactive agent is released into the cell. Preferably, the method also includes electrostatically binding a stabilizing agent to the lipid bilayer of the fusogenic liposome.

BRIEF DESCRIPTION OF THE DRAWINGS

FIG. 2 depicts the quantitation of enhanced transfection efficiency for charge reversal liposomes when targeted by modules with transferrin or folate.

FIG. 3 demonstrates that enhanced transfection efficiency of fusogenic N-acyl-PE liposomes by a folate targeting module is dependent on folate.

FIG. 4 demonstrates that folate targeting modules electrostatically linked to the liposomes enhance transfection more than folate conjugated to lipids.

FIG. 5 depicts the maintenance of liposomal integrity when an antibody conjugate is electrostatically bound to the liposome surface.

FIG. 6 demonstrates enhanced liposomal uptake mediated by an antibody conjugate electrostatically bound to the liposome surface.

FIG. 7 shows enhanced transfection as a result of increasing amounts of an antibody conjugate electrostatically bound to the surface of liposomes containing plasmid DNA.

FIG. 9 depicts the binding of transferrin-targeted liposomes of the present invention to OVCAR-3 cells in the presence and absence of serum.

FIG. 10 depicts the effect of polylysine-transferrin congugates on liposome binding and transfection.

FIG. 13 depicts the transfection efficiency of conjugates compared to free polylysine.

FIG. 15 demonstrates the beta-galactosidase assay for in vivo transfection.

DETAILED DESCRIPTION OF THE INVENTION

Figure 1A:
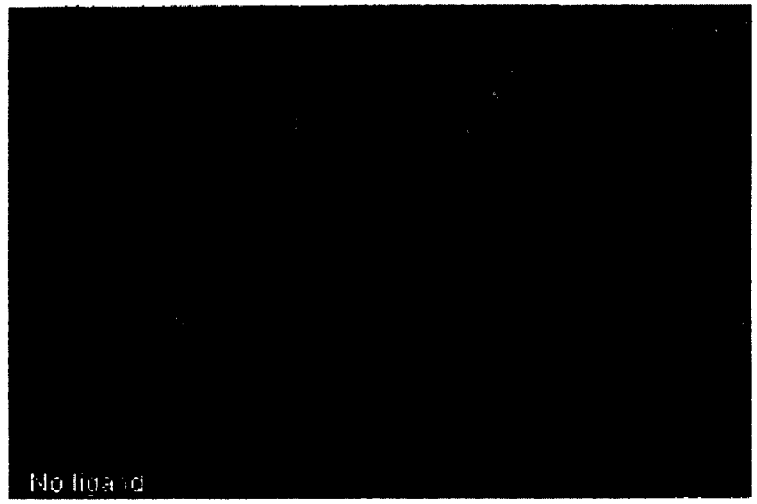
FIG. 1 depicts transfection of ovarian cancer cells by charge reversal liposomes and its enhancement by the use of a targeting/stabilizing module.

Delivery of liposomally encapsulated drugs or nucleic acids to specific cells via membrane fusion is a highly desirable goal because of protection of the cargo from degradation, potential for targeting and decrease of drug toxicity. Furthermore, it is advantageous to protect and/or stabilize the liposome itself until it reaches its desired site of delivery, because the liposome can be degraded in vivo. However, many targeting molecules such as antibodies and most protecting or stabilizing moieties such as polyethylene glycol (PEG) sterically inhibit the interaction between the liposomal membrane and the cell membrane, even though the liposome has bound to the cell surface. Because of this steric hindrance, it is generally not possible for fusogenic liposomes to efficiently deliver contents to the cytoplasm of the cell. This invention provides a targeted liposome, or targeted and stabilized liposome, where at least a portion of the targeting/stabilizing moieties are at least temporarily removable at the target site. The invention involves non-covalent adherence of a targeting moiety, and preferably a stabilizing moiety, to the surface of a liposome by electrostatic interactions, preferably multivalent electrostatic interactions. Such interactions can be quite strong if the valency of interaction is high enough. However, the reduced pH (relative to the extra-cellular plasma beyond the immediate vicinity of the cell) at certain in vivo sites such as the site of infection, inflammation or within certain cellular organelles or compartments such as endosomes, loosens or, in certain cases, reverses the interaction between the adherent moiety and the liposome. Once a fusogenic liposome, so modified, binds to the targeted cell type and encounters the reduced pH environment, the targeting/stabilizing moiety may be completely or partially removed if at least one of the electrostatically interacting species, i.e., membrane lipids or targeting/stabilizing agent is at least partially neutralized by the low pH environment in combination with other ions. Furthermore, a portion of the electrostatically bound targeting/stabilizing agent may exchange onto the cellular membrane following binding of the liposome and internalization into an endosome, also eliminating steric interference to fusion. For example, a fusogenic, anionic liposome can be protected by a polylysine conjugate with PEG and further targeted by a linked molecule, such as folate, transferrin or an antibody. If the anionic lipid is at least partially neutralized at lower pH, the targeting/stabilizing agent may completely or partially dissociate allowing exposure of the bare fusogenic liposomal membrane and subsequent fusion or partial fusion of the liposome with the endosomal membrane. This releases the liposomal contents into the cytoplasm. The contents may include any therapeutically relevant molecule(s).

A second advantage of this method of targeting and stabilizing the liposome is that a single type of liposome can be produced to which any number of targeting/stabilizing agents can be subsequently bound electrostatically. This embodiment merely requires mixing a fusogenic liposome, encapsulating a relavant drug or bioactive agent, with a linking moiety covalently bound to a targeting moiety that will bind to the specific targeted site. Thus, the system is modular. Selected targeting agents covalently linked to linking moieties that will bind electrostatically to the lipid bilayer can be prepared. Fusogenic liposomes encapsulating different drug or bioactive agents can be independently prepared. Then, depending on the target site and the therapeutic agent(s) one desires to administer, the appropriate combination of targeting agent and liposome encapsulating bioactive agent or drug can be mixed to provide a specific therapeutic agent that is targeted to the specific cellular site. This will allow patient-specific targeting with a single type of liposomal preparation that can be modified by an array of targeting agents.

The basic elements of the invention are a fusogenic liposome, a linking moiety and a targeting moiety. The fusogenic liposome comprises a lipid bilayer encapsulating contents to be delivered to the cytoplasm of a cell, the contents preferably being a bioactive agent, and more preferably condensed DNA. The targeting moiety is positioned exteriorly of the liposome, and is covalently bound to the linking moiety. The linking moiety is electrostatically bound to the lipid bilayer of the fusogenic liposome, thus indirectly linking the targeting moiety electrostatically to the lipid bilayer. Preferably, the invention also comprises a stabilizing moiety which, like the targeting moiety, is indirectly electrostatically bound to the lipid bilayer through a linking moiety. Specifically, the stabilizing moiety is covalently bound to the linking moiety, and the linking moiety is electrostatically bound to the lipid bilayer of the fusogenic lipid. A targeting moiety may be covalently bound to the stabilizing moiety. These individual elements of the invention will now be described in detail.

"Liposomes" are self-assembling structures comprising one or more lipid bilayers, each of which comprises two monolayers containing amphipathic lipid molecules oppositely oriented. Amphipathic lipids comprise a polar (hydrophilic) headgroup region covalently linked to one or two non-polar (hydrophobic) acyl chains. Energetically unfavorable contacts between the hydrophobic acyl chains and the surrounding aqueous medium induce the amphipathic lipid molecules to arrange themselves such that their polar headgroups are oriented towards the bilayer's surface, while the acyl chains reorient towards the interior of the bilayer. An energetically stable structure is thus formed in which the acyl chains are effectively shielded from coming into contact with the aqueous environment. A "fusogenic" liposome as defined herein is a liposome that is capable of interacting with a cell membrane in a way that permits the contents of the liposome to enter the cytoplasm of the cell. Without limitation, this interaction can take the form of complete or partial fusion of the membranes, or adjacent, contemporaneous and localized disruptions of the cellular and liposomal membranes that allows passage of the liposome contents into the cytoplasm of the cell.

Liposomes (see, e.g., Cullis et al., 1987; New, 1995) can have a single lipid bilayer (unilamellar liposomes, "ULVs"), or multiple lipid bilayers (multilamellar liposomes, "MLVs" or "SPLVs"). Each bilayer surrounds, or encapsulates, an aqueous compartment. Given this encapsulation of aqueous volume within a protective barrier of lipid molecules, liposomes are able to sequester encapsulated molecules, e.g., nucleic acids, away from the degrading effects of factors, e.g., nuclease enzymes, present in the external environment.

Liposomes can have a variety of sizes, e.g., an average diameter as low as 25 nm or as high as 10,000 nm or more. Size is affected by a number of factors, e.g., lipid composition and method of preparation, well within the purview of ordinarily skilled artisans to determine and account for, and is determined by a number of techniques, such as quasi-elastic light scattering, also within the artisans' purview.

Various methodologies, also well within the purview of ordinarily skilled artisans, such as sonication, homogenization, French Press application and milling can be used to prepare liposomes of a smaller size from larger liposomes. Extrusion (see, e.g., U.S. Pat. No. 5,008,050) can be used to size reduce liposomes, that is to produce liposomes having a predetermined mean size by forcing the liposomes, under pressure, through filter pores of a defined, selected size. Tangential flow filtration (WO89/008846), can also be used to regularize the size of liposomes, that is, to produce a population of liposomes having less size heterogeneity, and a more homogeneous, defined size distribution. The contents of these documents are incorporated herein by reference.

Liposomes of this invention can be unilamellar, or oligolamellar, and can have a size equal to that of liposomes produced by any of the methods set forth hereinabove. However, in preferred embodiments of this invention, the liposomes are unilamellar liposomes having number average sizes of about 50–500 nm.

Liposomes are composed of a variety of lipids, both amphipathic and nonamphipathic, obtained from a variety of sources, both natural and synthetic. Suitable liposomal lipids include, without limitation, phospholipids such as phosphatidylcholines ("PC's"), phosphatidylethanolamines ("PE's"), phosphatidylserines ("PS's"), phosphatidylglycerols ("PG's"), phosphatidylinositols ("PI's") and phosphatidic acids ("PA's"). Such phospholipids generally have two acyl chains, these being either both saturated, both unsaturated or one saturated and one unsaturated; said chains include, without limitation: myristate, palmitate, stearate, oleate, linoleate, linolenate, arachidate, arachidonate, behenate and lignocerate chains.

Phospholipids can also be derivatized, by the attachment thereto of a suitable reactive group. Such a group is generally an amino group, and hence, derivatized phospholipids are typically phosphatidylethanolamines. The different moieties suited to attachment to PE's include, without limitation: acyl chains (WO98/16199), useful for enhancing the fusability of liposomes to biological membranes; peptides (WO98/16240), useful for destabilizing liposomes in the vicinity of target cells; biotin and maleimido moieties (U.S. Pat. Nos. 5,059,421 and 5,399,331, respectively), useful for linking targeting moieties such as antibodies to liposomes; and, various molecules such as gangliosides, polyalkylethers, polyethylene glycols and organic dicarboxylic acids (see, e.g., U.S. Pat. Nos. 5,013,556, 4,920,016 and 4,837,028). The contents of the above-cited documents are incorporated herein by reference.

Accordingly, in the most preferred embodiments of this invention, the liposomes comprise a derivatized phospholipid, adapted so as to enhance delivery of their contents. The liposomes may also, but are not required to, comprise additional lipids as well, said additional lipids being incorporated into the liposomes for a number of reasons apparent to artisans of ordinary skill in the field of liposomology. Such reasons include, without limitation, stabilizing or targeting the liposomes, as well as further altering the liposomes' pharmacokinetic behavior. Suitable additional lipids include any of those lipids commonly recognized as suitable for incorporation in liposomes, including, without limitation, phospholipids, glycolipids and sterols.

Preferably, liposomes of this invention have a lipid component which comprises a derivatized phospholipid and an additional lipid. Suitable liposomes and the methods of preparing them are described in U.S. patent application Ser. No. 08/951,056, incorporated herein in its entirety by reference.

Preferably, the derivatized phospholipid is an N-acylated PE. Such NAPEs are useful in preparing fusogenic liposomes and are preferred for preparing liposomes comprising the drug or bioactive agent complexes of the present invention.

NAPE-induced bilayer destabilization induces the bilayers to fuse to biological membranes in the vicinity and hence, enhances the bilayers' fusogenicity (Shangguan et al., 1998). Enhanced fusogenicity, in turn, can be used to deliver encapsulated bioactive agents, such as nucleic acids or other agents that can not cross the cell membrane, to cells, by combining the cells with the liposomes under conditions, e.g., the presence of appropriate concentrations such as $Ca^{2+}$ and $Mg^{2+}$. Liposome-cell contact results in release of the liposome-encapsulated bioactive agents local to the cells, and/or directly into the cells' cytoplasm as a result of fusion between liposome and cell membranes. Such delivery is either in vivo or in vitro.

An alternative preferable formulation of liposomes for modular targeting are referred to below (example 1) as "charge reversal" liposomes. The composition of such liposomes also allows electrostatically bound targeting/stabilizing groups. Such liposomes reverse charge at low pH, dissociating the targeting/stabilizing conjugates and attaining a positive charge to enhance interaction with the cellular membrane.

The liposomal lipid can also comprise a "headgroup-modified lipid," i.e., a lipid having a polar group derivatized by the attachment thereto of a moiety capable of inhibiting the binding of serum proteins to a liposome incorporating the lipid. Incorporation of headgroup-modified lipids into liposomes thus alters their pharmacokinetic behavior, such that the liposomes remain in the circulation of an animal for a longer period of time then would otherwise be the case (see, e.g., Blume et al., 1993; Gabizon et al., 1993; Park et al., 1992; Woodle et al., U.S. Pat. No. 5,013,556; Allen et al., U.S. Pat. Nos. 4,837,028 and 4,920,016; the contents of these documents being incorporated herein by reference).

Nucleic acids that may be encapsulated in the liposome are DNA, including genomic DNA, plasmid DNA and cDNA, or RNA; preferably, the encapsulated nucleic acid is DNA, more preferably, closed (circular) plasmid DNA. "Encapsulated" or "containing" as used herein with regard to the contents of the liposome describes materials that are within the interior aqueous volume of the liposome, intercalated in the lipid bilayer of the liposome, or partly intercalated in the lipid bilayer of the liposome.

Liposomes of the invention can contain one or more bioactive agents. Bioactive agents which may be associated with liposomes include, but are not limited to: antiviral agents such as acyclovir, zidovudine and the interferons; antibacterial agents such as aminoglycosides, cephalosporins and tetracyclines; antifungal agents such as polyene antibiotics, imidazoles and triazoles; antimetabolic agents such as folic acid, and purine and pyrimidine analogs; antineoplastic agents such as the anthracycline antibiotics and plant alkaloids; sterols such as cholesterol; carbohydrates, e.g., sugars and starches; amino acids, peptides, proteins such as cell receptor proteins, immunoglobulins, enzymes, hormones, neurotransmitters and glycoproteins; dyes; radiolabels such as radioisotopes and radioisotope-labeled compounds; radiopaque compounds; fluorescent compounds; mydriatic compounds; bronchodilators; local anesthetics; and the like.

Liposomal bioactive agent formulations can enhance the therapeutic index of the bioactive agent, for example by buffering the agent's toxicity. Liposomes can also reduce the rate at which a bioactive agent is cleared from the circulation of animals. Accordingly, liposomal formulation of bioactive agents can mean that less of the agent need be administered to achieve the desired effect.

The liposome of this invention may be dehydrated, stored and then reconstituted such that a substantial portion of their internal contents are retained. Liposomal dehydration generally requires use of a hydrophilic drying protectant such as a disaccharide sugar at both the inside and outside surfaces of the liposomes' bilayers (see U.S. Pat. No. 4,880,635, the contents of which are incorporated herein by reference). This hydrophilic compound is generally believed to prevent the rearrangement of the lipids in liposomes, so that their size and contents are maintained during the drying procedure, and through subsequent rehydration. Appropriate qualities for such drying protectants are that they be strong hydrogen bond acceptors, and possess stereochemical features that preserve the intermolecular spacing of the liposome bilayer components. Alternatively, the drying protectant can be omitted if the liposome preparation is not frozen prior to dehydration, and sufficient water remains in the preparation subsequent to dehydration.

Also provided herein is a pharmaceutical composition comprising a pharmaceutically acceptable carrier and the liposome of this invention. Said composition is useful, for example, in the delivery of nucleic acids to the cells of an animal. "Pharmaceutically acceptable carriers" as used herein are those media generally acceptable for use in connection with the administration of lipids and liposomes, including liposomal bioactive agent formulations, to animals, including humans. Pharmaceutically acceptable carriers are generally formulated according to a number of factors well within the purview of the ordinarily skilled artisan to determine and account for, including without limitation: the particular liposomal bioactive agent used, its concentration, stability and intended bioavailability; the disease, disorder or condition being treated with the liposomal composition; the subject, its age, size and general condition; and the composition's intended route of administration, e.g., nasal, oral, ophthalmic, topical, transdermal, vaginal, subcutaneous, intramammary, intraperitoneal, intravenous, or intramuscular (see, for example, Nairn (1985), the contents of which are incorporated herein by reference). Typical pharmaceutically acceptable carriers used in parenteral bioactive agent administration include, for example, D5W, an aqueous solution containing 5% weight by volume of dextrose, and physiological saline. Pharmaceutically acceptable carriers can contain additional ingredients, for example those which enhance the stability of the active ingredients included, such as preservatives and antioxidants.

Lipids useful in the practice of this invention are, as described hereinabove, those lipids recognized as suitable for incorporation in liposomes, either on their own or in connection with additional lipids; these include, phospholipids, glycolipids, sterols and their derivatives. Organic solvents used in this method are any of the variety of solvents useful in dissolving lipids during the course of liposome preparation; these include, without limitation, methanol, ethanol, dimethylsulfoxide, chloroform, and mixtures thereof. Preferably, the organic solvent is chloroform or methylene chloride.

Still further provided herein is a method of transfecting the cells of an animal with a targeted fusogenic liposome comprising one or more bioactive agents such as, but not limited to, a nucleic acid. The method comprises the steps of preparing a fusogenic liposome encapsulating a bioactive agent; preparing a targeting moiety covalently bound to a linking agent said linking agent being capable of electrostatically binding to said fusogenic liposome at normal physiological pH, mixing the loaded fusogenic liposome with the targeting conjugate and contacting the cells with the composition comprised of the loaded fusogenic liposome electrostatically bound to the targeting agent. Such contact is either in vitro, in which case, a composition comprising the liposome is added to the culture medium surrounding the cells, or in vivo, in which case the liposome is administered in a pharmaceutical composition also comprising a pharmaceutically acceptable carrier, and is administered to the animal by any of the standard means of administering such compositions to animals.

The targeting moiety of the invention can be any chemical composition that favors the positioning of a liposome to a specific site or sites. More than one targeting moiety may be utilized on a single liposome. Preferably, the targeting moiety is selected from the group consisting of a vitamin such as folate; transferrin; an antibody such as OVB-3, anti-CA125, anti-CEA, and others; sialyl Lewis X antigen, hyaluronic acid, mannose derivatives, glucose derivatives, cell specific lectins, galaptin, galectin, lactosylceramide, a steroid derivative, an RGD sequence, a ligand for a cell surface receptor such as epidermal growth factor (EGF), EGF-binding peptide, urokinase receptor binding peptide, a thrombospondin-derived peptide, an albumin derivative and/or a combinatorial molecule directed against various cells.

The linking moiety can be any chemical composition that is capable of simultaneously binding to the lipid bilayer of a liposome electrostatically and binding to a targeting or stabilizing moiety covalently, such that the electrostatic bond can be so weakened in reduced pH environment (relative to the extra-cellular plasma not in the immediate vicinity of the cell) so that at least some of the linking moiety at least temporarily dissociates from the liposome, thereby exposing at least a portion of the outer lipid bilayer for at least some period of time. The linking moiety is preferably a small molecule that does not hinder the interaction between the targeting moiety and targeted cell. More than one linking moiety can be used on a single liposome, and the linking moieties used to bind the targeting and stabilizing moieties may be the same or different. Preferably, the linking moiety is selected from the group consisting of polylysine, protamine, polyethyleneimine, polyarginine, polyacrylate, a spermine derivative, cytochrome c, an annexin, heparin sulfate, an aminodextran, polyaspartate, polyglutamate, a polysialic acid, and/or poly(2-ethylacrylic acid).

The stabilizing moiety of the invention is any chemical composition that inhibits or prevents a liposome from fusing with other liposomes or non-target cells, and/or protects the lipid bilayer of the liposome from the disruptive, degrading or interfering action of detrimental compounds (e.g. serum proteins). More than one stabilizing moiety may be used on a single liposome. Preferably, the stabilizing moiety is selected from the group consisting of polyethylene glycol, polyvinylpyrrolidone, a dextran, a polyamino acid, methylpolyoxazoline, polyglycerol, poly(acryloyl morpholine), and/or polyacrylamide.

Preferred embodiments of the invention will now be described in the Examples below. The Examples are intended to be illustrative of the invention and are not intended to limit the scope of the invention defined in the appended claims.

EXAMPLE 1

Formulations

Preparation of Liposomes for Delivery of Nucleic Acids:

Preferably, for the delivery of nucleic acids to cells, liposomes are prepared according to the method described in U.S. Provisional Application Ser. No. 60/122,365 entitled "Encapsulation of Bioactive Complexes in Liposomes", filed on Mar. 2, 1999. One embodiment is described below.

Plasmid Purification: Two plasmids were used in this study: the pZeoSVLacZ plasmid which is 6.5 kb, and expresses the lacZ gene for β-galactosidase in mammalian cells from the SV40 early enhancer-promoter, allowing selection in mammalian cells and $E.$ $coli$ using the antibiotic zeocin; and, the pEGFP-C1 plasmid, which is 4.7 kb and expresses enhanced green fluorescent protein (EGFP) from a human cytomegalovirus immediate early promoter, allowing selection in $E.$ $coli$ using kanamycin, and in mammalian cells using G418. Plasmids were purified from $E.$ $Coli$ (Baumann and Bloomfield, 1995; or by Qiagen kit per manufacturer's instructions (Qiagen, Valencia, Calif.))13 the final ratio of O.D. at 260 nm to O.D. at 280 nm was greater than 1.9 for all preparations; agarose gel electrophoresis indicated DNA in the expected size range.

Preparation of Liposomal-DNA formulations (fusogenic N-acyl-PE liposomes; two step emulsion method): Samples were prepared by diluting 200 μg of DNA into 125 μl of low salt buffer (LSB; 10 mM Tris HCl, 1 mM NaCl, pH 7.0, all LSB used in these preparations also contained 200 mM sucrose), and then combining the resulting suspension with 1 ml CHCl$_3$ containing 30 μmole of 70:30 molar ratio of N—C12 DOPE and DOPC, in a 13×100 Pyrex tube while vortexing. The sample was immediately sonicated for 12 seconds in a bath sonicator (Laboratory Supplies Co. Hicksville, N.Y.) under maximum power, to form an emulsion with plasmid DNA first. Subsequently, a 125 μl aliquot of LSB containing spermine (preferably 16 to 40 millimolar) was added to this emulsion with vortexing and sonication.

Resulting emulsions were placed, within a few minutes, in a flask on a Rotovap (Büichi Laboratoriums-Technik AG, Switzerland). Organic solvent was removed while rotating the flask at its maximum rate, while the vacuum was modulated with a pin valve. Initially a vacuum of approximately 600–650 mm was established, this being subsequently increased, as rapidly as possible without excessive bubbling, until the maximum vacuum was reached (approximately 730 mm); the flask was then evacuated for another 25 minutes. The film left on the flask was resuspended in 1 ml of 300 mM sucrose in LSB, and the sample was extruded five times through 0.4 μm polycarbonate membrane filters (Poretics, Livemore, Calif.). The sample was then dialyzed against Hank's balanced salt buffer (HBSS) without $Ca^{2+}$/$Mg^{2+}$, overnight at 4° C.

After preparation of the nucleic acid-containing liposomes described above, the free plasmid DNA was separated from liposome-encapsulated DNA by centrifugation. The liposomes were pelleted and washed prior to forming the targeting complex. The preparations may be scaled-up to produce larger amounts of product by methods known in the art.

Preparation of Charge Reversal Liposomal DNA Formulations:

In another embodiment, liposomes, heretofore referred to as charge reversal liposomes, were made by first mixing the lipids in chloroform (DOPC:POPE:cholesterol:cholesteryl hemisuccinate:DOPAP:oleyl actetate, 12:50:2.5:12.5:10.5: 10.5). Next, plasmids were condensed with spermine using the two-step lipid emulsion protocol previously described in the embodiment above. One difference is that the final sucrose concentration in the DNA solution to be encapsulated was 300 mM. Solvent was removed by either rotary evaporation or sparging with nitrogen. The liposomes were suspended from the resulting paste in 300 mM sucrose, extruded through 0.4 µm filters, then dialyzed against PBS or Hanks balanced salt solution (HBSS). Unencapsulated plasmid was removed by centrifuging the sample at 10,000 g. The liposome/plasmid pellet was washed, respun and resuspended in PBS or HBSS. The size distribution of the liposomes was determined by light scattering using a NICOMP model 370 submicron particle sizer (NICOMP, Santa Barbara, Calif.). The amount of plasmid present in the liposomal pellet was quantitated using a PicoGreen fluorescent assay (Molecular Probes, Inc., Eugene, Oreg.) as described in Example 3 "Assays".

Liposomes of this composition were characterized by transmission electron microscopy of a liposome/plasmid preparation with polylysine-anti-OVB3 ligand attached. The sample was placed on a carbon coated EM grid and negatively stained with 1% uranyl acetate. Liposomes of a heterogenous size were observed with varying amounts of stain penetration. The final liposome/plasmid preparations gave a Gaussian size distribution by light scattering analysis. The number weighted mean diameter of 7 different preparations was 140 nm±20 nm (standard deviation of the mean for any single preparation ranged between 40–55%). Plasmid content in the washed liposome/plasmid samples ranged from 1.25–2.45 µg DNA/mol lipid, with a mean of 1.6 µg DNA/µmol lipid. This plasmid fraction was protected from digestion with DNAse I suggesting either encapsulation or very tight association with the liposomes.

EXAMPLE 2

Synthesis of Targeting/Stabilizing Moiety-Linker Conjugates

Targeting/stabilizing modules were synthesized to use with liposomes prepared as in example 1. Targeting/stabilizing moieties may be covalently coupled to a linker for electrostatic interaction, such as polylysine (pK), by any method known in the art. Examples of processes for coupling polylysine to targeting agents such as folic acid, transferrin and antibodies are provided herein for exemplary purposes only. Methods for coupling a linking agent such as polylysine to a stablizing agent such as PEG or to a stabilizing agent and a targeting moiety are also provided herein.

a. Preparation of Folic acid, PEG and Polylysine Without Glutaric Acid (FA-NH-PEG-CO-PL or FPK)

Preparation of FAA

Folic acid (50 mg, 0.11 mmole) was dissolved in 6 ml of DMF:PY (5:1; v/v). To this solution dicylohexylcarbodiimide (DCC, 140 mg, 0.68 mmoles) was added and the reaction mixture was stirred at room temperature for 2–3 h. Dicyclohexylurea (DCU) precipitate developed with time.

Deprotection of Boc Group from BocNH-PEG-CO$_2$NHS

BocNH-PEG-CO$_2$NHS (3400 m.w., Shearwater Polymers, Huntsville, Ala.) was dissolved in 5 ml of CH$_2$Cl$_2$: TFA (4:1%,v/v) solution. This mixture was stirred at room temperature for 2 hours. TLC analysis revealed that the reaction had gone to completion. The product gave a positive ninhydrin test. The solvents were removed under reduced pressure and the sample dried under high vacuum.

Coupling FA to NH$_2$-PEG-CO NHS

To the FAA reaction mixture, H$_2$N-PEG-CO$_2$NHS (186 mg, 0.057 mmole) was added in 2.5 ml of DMF:triethylamine (100:1 v/v) and the reaction mixture was stirred at room temperature overnight. TLC analysis showed that the reaction had gone to completion. The product was UV and ninhydrin positive. Solvents were removed from the reaction mixture under reduced pressure and the sample dried under high vacuum.

Coupling FA-NH-PEG-CO$_2$NHS to Polylysine

To a solution of FA-NH-PEG-CO2NHS (100 mg, 0.027 mmole) in 5 ml of DMF:Py (4:1 v/v), were added PLL (62.15 mg, 0.0224 mmole) and Et$_3$N (3.4 mg, 4.7 ul, 0.0336 mmole). The reaction mixture was stirred at room temperature overnight. At this time point TLC analysis revealed that a new polar spot was formed which was UV positive and gave a positive ninhydrin test. Solvents were removed from the reaction mixture under reduced pressure and the sample dried under high vacuum. The residual material was suspended in CHCl$_3$ and spun at 4000 rpm for 30 min. The supernatant solid material was separated and washed with CHCl$_3$. Pure Sample weight 55.4 mg (37.5% Yield).

Conjugates of folate or PEG directly linked to polylysine or other charged molecules may also be prepared by similar procedures.

b. Preparation of Folate-PEG-Polylysine (FA-PEG-GA-PL or FPGK) Using Glutaric Acid Preparation of Folic Acid Anhydride (FAA)

Folic acid (50 mg, 0.11 mmole) was dissolved in 6 mL of N,N-dimethylformamide:pyridine (DMF:PY) (4:1 v/v). To this solution was added dicyclohexocarbodiimide (DCC) (140 mg, 0.68 mmole) and the reaction mixture was stirred at room temperature for ~3 h. With time dicyclohexylurea (DCU) precipitate was observed in reaction mixture.

Coupling FA to PEG (3400)

To the FAA reaction mixture prepared above, H$_2$N-PEG-NHBoc (3400 m.w. Shearwater Polymers, Huntsville, Ala.) (192 mg, 0.057 mmole) was added in 1 ml of N,N-dimethylformamide. This reaction mixture was stirred at room temperature overnight. At this point TLC analysis revealed that the reaction had gone to completion. The product formed was UV positive and gave a negative ninhydrin test. Solvents were removed under reduced pressure.

Deprotection of boc Group from FA-NH-PEG-NHBoc

The residual material was dissolved in 5 ml of CH$_2$Cl$_2$: TFA (4:1 v/v) and the reaction mixture was stirred at room temperature for 2–3 hr. At this time point, TLC analysis revealed that the reaction had gone to completion. The product was UV positive and gave a positive ninhydrin test. Solvents were removed at reduced pressure and the residual material dried under high vacuum.

Introduction of GA Molecule (FA-NH-PEG-NH—CO(CH2)$_3$COOH)

The residual material was dissolved in 5 ml of DMF:Py (4:1 v/v). To this solution Et$_3$N (15.7 µl, 11.41 mg, 0.113 mmole) and Glutaric anhydride (9.7 mg; 0.085 mmole) were added and the reaction mixture was stirred at room temperature overnight. TLC analysis showed that the reaction had gone to completion. TLC analysis was performed in CHCl$_3$:CH$_3$OH:H$_2$O (65:30:5; v/v/v). The product gave a negative ninhydrin test. The residual weight of the sample was 649 mg.

Coupling Polylysine (PL) (FA-NH-PEG-NH—CO(CH$_2$)$_3$CO-PL):

DCC (44 mg, 0.21 mmole) was added to a solution of FA-NH-PEG-NH—CO(CH$_2$)$_3$COOH (residual material) (162 mg, 0.043 mmole) in 4 ml of DMSO:Py (4:1 v/v). This mixture was stirred at room temperature for 2–3 hrs. With time DCU precipitate developed. At this point polylysine HBr (32 mg, 0.011 mmole) was added to the reaction mixture in 1.4 ml of DMSO:Py:Et$_3$N (1000:200:200 µl) solution. This reaction mixture was stirred at room temperature overnight. At this time point TLC analysis in CHCl$_3$:CH$_3$OH:H$_2$O (60:35:5 v/v/v) revealed that the reaction had gone to completion. TLC analysis gave positive UV and ninhydrin tests. Solvents were removed under reduced pressure. The residual material was dissolved in CHCl$_3$ and the precipitate separated by spinning at 3000–4000 rpm for 30 minutes. The solid mixture was separated and washed with CHCl$_3$. The pure sample weighed 19.1 mg (27% Yield).

c. Preparation of Folate-PEG-Protamine (FA-PEG-GA-Pro or FPGPr) Using Glutaric Acid FA-PEG-GA was prepared as described in part b in the Folate-PEG-Polylysine synthesis scheme.

Coupling Protamine to (FA-NH-PEG-NH—CO(CH$_{23}$CO-Protamine):

DCC (8.03 mg, 0.039 mmole) was added to a solution of FA-NH-PEG-NH—CO(CH$_2$)$_3$COOH (residual material) (50 mg, 0.013 mmole) in 3.0 ml of CHCl$_3$. This mixture was stirred at room temperature for 2–3 hrs. At this point protamine free base (13.3 mg, 0.0033 mmole) was added to the reaction mixture in 1.5 ml of 1,1,1,3,3,3-hexafluoroisopropanol. This reaction mixture was stirred at room temperature overnight. At this time point TLC analysis in CHCl$_3$:CH$_3$OH:H$_2$O (60:35:5 v/v/v) revealed that the reaction had gone to completion. TLC analysis gave positive UV and ninhydrin tests. Solvents were removed under reduced pressure. The residual material was dissolved in CHCl$_3$ and the precipitate separated by spinning at 3000–4000 rpm for 30 minutes. The solid mixture was separated and washed with CHCl$_3$. The pure sample weighed 5.5 mg (22% Yield).

Conjugates of folate alone or PEG alone directly linked to polylysine or other charged molecules may also be prepared by minor modifications of this method.

d. Preparation of Acetyl-PEG-Protamine (Ac-PEG-GA-Pro or AcPGPr) Using Glutaric Acid Several variations of the PEG conjugates were prepared as controls to compare with the above conjugates. These were missing one of more component of the active conjugate. The Ac-PEG-GA-Pro conjugate, or AcPGPr, was prepared by substituting an acetyl group for folate on the conjugate. It was, therefore, not targeted to a cell receptor.

In addition to control experiments, it may be desirable to use such a non-targeted protecting moiety to modulate the liposomal surface for optimal targeting in vivo. For instance, a non-targeted conjugate may be used in addition to a targeting conjugate on the liposomal surface.

Acetylation of NH$_2$—PEG-NHBOC:

To a solution of H$_2$N-PEG-NHBOC (100 mg, 0.0294 mmole) in 3.0 mL of CHCl$_3$ were added acetic anhydride (9.0 mg, 7.85 µL, 0.088 mmole) and excess amount of TEA. This reaction mixture was sealed under nitrogen and stirred at room temperature for 3–4 h. At this time point TLC analysis in CHCl$_3$:CH$_3$OH (9:1 v/v) revealed that the reaction had gone to the completion. TLC analysis gave negative Ninhydrin test. Solvents were removed under reduced pressure and residual material was used in next step without purification.

Deprotection of BOC gp from Ac-NH-PEG-NHBOC:

To a solution of Ac-NH-PEG-NHBOC in 2.2 mL of CH$_2$Cl$_2$ was added 0.25 mL of TFA. This reaction mixture was stirred at room temperature for 2 h. At this time point TLC analysis in CHCl$_3$:CH$_3$OH (9:1 v/v) revealed that the reaction had gone to the completion. TLC analysis gave positive ninhydrin test. Solvents were removed under reduced pressure and residual material used in the next step without purification.

Introduction of GA Molecule on Ac-NH-PEG-NH$_2$:

The residual material was dissolved in 3.0 mL of CHCl$_3$. To this solution excess amount of Et$_3$N and Glutaric anhydride (5 mg; 0.044 mmole) were added and the reaction mixture was stirred at room temperature overnight. TLC analysis showed that the reaction had gone to completion. TLC analysis was performed in CHCl$_3$:CH$_3$OH (9:1 v/v). The product gave a negative ninhydrin test. The residual material was used in the next step without further purification.

Coupling Ac-NH-PEG-NH—CO—(CH$_2$)$_3$, —COOH to Protamine (Pr):

To a solution of Ac-NH-PEG-NH—CO—(CH$_2$)$_3$—COOH in 2.0 mL of CHCl$_3$ was added DCC (18.2 mg, 0.088 mmole) and the reaction mixture was stirred at room temperature for 2–3 h. At this time point white ppte was developed. Protamine (30.0 mg, 0.0074 mmol) in 1.6 mL of 1,1,1,3,3,3 Hexafluoro isopropyl alcohol was added to the reaction mixture and the reaction mixture was stirred at room temperature over night. At this time point, TLC analysis gave a polar positive spot. Solvents were removed under reduced pressure and residual material was suspended in CHCl$_3$. The suspension was centrifuged at 3500 rpm for 15 min. The solid material was separated from clear solution to give 23 mg, yielding 35%.

e. Characterization of the Amine Content of Protamine and Polylysine Conjugates with PEG and Folate or an Acetyl Group The ratio of protamine or polylysine to the remaining molecular mass in the final products was characterized by fluorescent derivatization of free amino groups with fluorescamine, a reagent that becomes fluorescent upon reaction with amines. As a calibration of fluorescence response, weighed amounts of free polylysine or protamine were reacted with fluorescamine to yield a fluorescent product. Standard curves were prepared for either protamine or the 3,000 molecular weight polylysine molecule used for conjugate formation. The concentration of amines in the conjugates was then determined by reaction with fluorescamine. The assay was done in a 96 well Cytofluor 4000 fluorescence plate reader (PerSeptive Biosystems, Cambridge, Mass.). After dilution of the sample into 50 µl total volume of water, 200 µl of 130 mM NaBH$_2$O$_3$ buffer at pH 9.5 and 50 µl 0.2 mg/ml fluorescamine which was dissolved in acetone were added. The samples were incubated at room temperature for 20 minutes after which the fluorescence was measured at 490±20 nm with 395±12 nm excitation. The fluorescence readings were compared to the standard curves to determine the amount of protamine or polylysine in a given weight of conjugate and the ratio of this amount to the total mass was calculated. For the protamine conjugates with PEG and either folate or an acetyl group the expected ratio of a 1:1 conjugate is 0.52 and 0.54, respectively, while determined ratios were 0.50±0.05 and 0.56±0.05, respectively. For the polylysine conjugates FPK and FPGK, the calculated ratios are 0.45 and 0.44, respectively, while the determined ratios were 0.64±0.17 and 0.35±0.05, respectively. Because of the polydispersity of the polylysine used for this purpose, these ratios are only approximate guidelines for the 1:1 complexes.

The protamine conjugates clearly contained a single protamine per PEG group, while the polylysine conjugates were close to the desired ratios.

f. Preparation of a Phospholipid Derivative of Folate and PEG, Folate-PEG-DOPE (FA-PEG-DOPE or FPPE)

A phospholipid conjugate of folate and PEG was prepared to compare to the conjugates of folate prepared above. The phospholipid conjugate would insert hydrophobically into the liposomal membrane, while the other conjugates would interact with the liposomal membrane via an electrostatic attraction. The results are further discusses in Example 8.

Coupling DOPE to t-BOCNH-PEG-CO$_2$NHS:

To a solution of DOPE (20 mg, 0.026 mmole) in 3.0 mL of CHCl$_3$ were added t-BocNH-PEG-CO$_2$NHS (91.5 mg, 0.026 mmole) and TEA (2.7 mg, 0.026 mmole). This reaction mixture was sealed under nitrogen and stirred at room temperature overnight. At this time point TLC analysis in CHCl$_3$:CH$_3$OH:H$_2$O (65:25:4 v/v) revealed that the reaction had gone to the completion. Solvents were removed under reduced pressure and residual material was purified on column chromatography to give 168 mg (53%). Some of characteristic $^1$H NMR (CDCl$_3$) signals are: δ 0.86 (t, 6H, J=6.35 Hz, CH$_3$), 1.25–1.27 (br, (CH$_2$)$_n$ for DOPE), 1.43 (s, t-BOC), 3.63 (br, CH$_2$'s for PEG) and 5.32 (br signal for olefinic protons).

Deprotection of t-BOC from t-BOCNH-PEG-DOPE Conjugate:

To a solution of t-BOCNH-PEG-NH-DOPE conjugate in 4.0 mL of CH$_2$Cl$_2$ was added 1.0 mL of TFA. This reaction mixture was stirred at room temperature for 2 h. At this time point TLC analysis in CHCl$_3$:CH$_3$OH:H$_2$O (65:25:4 v/v) revealed that the reaction had gone to the completion. Solvents were removed under reduced pressure and residual material was purified on column chromatography to give 44 mg. Some of characteristic $^1$H NMR (CDCl$_3$) signals are: δ 0.86 (t, 6H, J=6.11 Hz, CH$_3$), 1.25–1.27 (br, (CH$_2$)$_n$ for DOPE), 3.63 (br, CH$_2$'s for PEG) and 5.32 (br signal for olefinic protons).

Coupling FA to NH$_2$—PEG-DOPE:

To a solution of FA (10.58, 0.026 mmole) in 3.0 mL of DMSO:Py (2:1 v/v) were added DCC (14.8 mg, 0.072 mmole) and NH$_2$—PEG-DOPE (45 mg, 0.012 mmole). This reaction mixture was sealed under nitrogen and stirred at room temperature for overnight. At this time point TLC analysis in CHCl$_3$:CH$_3$OH:H$_2$O (75:35:6 v/v) revealed that the reaction had gone to the completion. TLC analysis gave positive UV, ninhydrin and molybdate tests. Solvents were removed under reduced pressure and residual material was purified on column chromatography to give 21.5 mg (43%). Some of characteristic $^1$H NMR (CDCl$_3$:CD$_3$OD 8:1 v/v) signals are: δ δ 0.79 (t, 6H, J=6.62 Hz, CH$_3$), 1.18–1.21 (br, (CH$_2$)$_n$ for DOPE), 3.56 (br, CH$_2$'s for PEG), 5.25 (br signal for olefinic protons) and 6.60–8.6 (3 signals for FA).

g. Coupling Antibody to Polylysine: Carbohydrate-Specific Polylysine Coupling to the Monoclonal IgG OVB-3

An antibody conjugate was also prepared for electrostatic linkage to liposomes to target such liposomes to the appropriate cells.

OVB-3 Isolation:

OVB-3 is a monoclonal (mab) IgG that binds specifically to human ovarian carcinoma cells. The hybridoma cell line was obtained from ATCC (HB-9147). Hybridoma cells were injected into Balb/c mice and ascites was collected a couple weeks later. The mab was isolated from the ascites using a Protein A column and stored in a phosphate buffer (150 mM NaCl, 20 mM NaP$_1$, pH 7.5)

Preparation of Thiolated Polylysine:

Free sulfhydryl groups were introduced on to polylysine polymers by modifying the amines with 2-iminothiolane (Traut's reagent). Hydrobromide polylysine in the 1,000 to 4,000 molecular weight range was obtained from SIGMA. The polylysine (45 mg) was dissolved in 1.0 ml of borate buffer (100 mM NaBH$_2$O$_3$ pH 8.0). To this solution, 1 ml of 95.9 mg/ml 2-iminothiolane dissolved in water was added. The mixture was incubated for 1 hour in the dark with gentle shaking. After incubation, the sample was transferred to a 30 ml glass centrifuge tube and 18 ml of isopropanol was added. The sample was centrifuged for 20 minutes at 9K RPM. The supernate was removed and the pellet was dried with a gentle stream of N$_2$. The pellet was redissolved in 2 ml of the pH 8.0 borate buffer.

Labeling the Polylysine with Alexa 350:

In order to provide a quantitative measure of the extent of mab to polylysine coupling, the thiolated polylysine was labeled with the fluorescent probe Alexa 350 carboxylic acid succinimidyl ester which was obtained from Molecular Probes. A 10 mg/ml Alexa 350 DMSO stock solution was prepared. Seventy-five μl of Alexa 350 stock solution was added to 2 ml of previously prepared thiolated polylysine sample. The sample was incubated in the dark at room temperature for 1 hour with gentle shaking. After incubation, the sample was transferred to a 30 ml glass centrifuge tube and 18 ml of isopropanol was added. The sample was centrifuged for 20 minutes at 9K RPM. The supernate was removed and the pellet was dried with a gentle stream of N$_2$. The sample was redissolved in 100 to 200 μl of water. The sample was freeze-dried in order to obtain the sample weight. Following the determination of the sample weight, the sample was dissolved in NaP$_1$ buffer (100 mM NaP$_1$, pH 7.0) at a concentration of 20 mg/ml.

Oxidation of the Mab by Periodate:

The polylysine coupling to OVB-3 was done at the carbohydrate region of the mab. Two hundred μl of 300 mM NaIO$_4$ in water was added to 2 ml of 5 mg/ml OVB-3 in 150 mM NaCl, 20 mM NaP$_1$ pH 7.5. The sample was incubated for 1 hour at room temperature in the dark. Glycerol (200 μl) was added to stop the oxidation reaction. The sample was then subjected to a PD-δ 0 Sephadex G-25 desalting column which was equilibrated with a pH 5.0 acetate buffer (100 mM Na Acetate, pH 5.0). The sample was reconcentrated back to 2 ml using an Amicon stirred ultrafiltration cell with 30K MWCO filter.

Coupling the Thiolated Polylysine to the Oxidized OVB-3:

The thiolated polylysine was linked to the carbohydrate oxidized OVB-3 using the heterobifunctional cross-linker MPBH (4-(4-N-maleimidophenyl)butyric acid hydrazide) which was obtained from Pierce. One hundred μl of an 80 mM DMSO MPBH stock solution was added to the previously prepared 2 ml oxidized OVB-3 solution (100 mM Na Acetate, pH 5.0). The final MPBH concentration was 4 mM. The sample was incubated for 2 hours at room temperature in the dark with gentle shaking. The sample was then run down a PD-δ 0 Sephadex G-25 desalting column which was equilibrated with a pH 7.0 $P_i$ buffer (100 mM $NaP_1$, pH 7.0). The OVB-3 column fractions were pooled and 15 mg of previously prepared thiolated polylysine (100 mM $NaP_1$, pH 7.0) was added. The sample was incubated at room temperature for at least 3 hours. The unreacted thiolated polylysine was separated from the OVB-3 polylysine conjugate by gel filtration on (Sephacryl-200 HR) or a Protein A column (Pharmacia Biotech HiTrap Protein A column) using a pH 7.4 TES buffer (150 mM NaCl, 10 mM TES, 0.1 mM EDTA, pH 7.4). The OBV-3 polylysine conjugate was pooled, reconcentrated by stirred ultrafiltration to a stock solution concentration of about 1 mg/ml, and stored in the refrigerator.

EXAMPLE 3

Assay Methods and Materials:

a. Cell Cultures for Measurements of Liposome Binding and Transfection

OVCAR-3 cells were plated at $2\times10^5$ cells per ml in 96-well plates in 0.1 ml per well of RPMI 1640 with 10% heat inactivated fetal bovine serum. Cells were allowed to grow for two days (approximately 40–48 hours) before transfections were performed; at this point the cells were at confluency. In the case of pH-dependent liposomes described below, the cells were allowed to grow for only one day before transfection.

b. Measure of Cell Number (CBAM, Calcein Blue Acetoxy Methyl Ester)

Cell number in terms of total intracellular esterase activity was determined by washing the cells with phosphate buffered saline (PBS), staining with calcein blue acetoxy methyl ester (CBAM-5 µM in PBS for approximately 30–45 minutes at room temperature), and then rinsing the plates with PBS). 100 µl/well of detergent solution (1% $C_{12}E_8$, TE, pH 8) was added to each well. Cell number was determined in a Cytofluor 2 instrument by determining the calcein blue fluorescence (excitation at 360 nm, emission at 460 nm, gain usually at 80). Plates were again washed 2 times with detergent solution and read again in the same detergent solution to correct for background. A series of unlabeled control wells were also read as an internal blank. All trnasfection (EGFP) and liposome binding (rhodamine) fluorescent readings were corrected by dividing by the CBAM readings.

c. Measurement of Binding of Liposomes to Cells

Liposomes comprising about 0.1 to about 1 mole % N-(lissamine rhodamine B sulfonyl) phosphatidylethanolamine were incubated with the cells and the rhodamine fluorescence was observed visually and by measurement on a Cytofluor II plate reader using 560 nm excitation and 620 nm emission.

d. Transfection Efficiency Assay

Transfection success, and expression of the transfected nucleic acid in a cell, can be detected in a number of ways, these generally depending upon either detection of the physical presence of the nucleic acid in the cell, e.g., by incorporation of radionucleotides in the nucleic acid, or by detecting expression of the protein encoded by the nucleic acid. This can be accomplished in a number of ways, including, without limitation, where the protein is a detectable, e.g., fluorescent, marker, or where the protein is a selectable, e.g., cytotoxic agent-resistance, marker.

For example, the plasmid pEGFP-1 contains a DNA sequence encoding the enhanced green fluorescence protein, whose presence is detected by fluorescence microscopy or fluorescence plate reader. Accordingly, successful transfection of cells with this plasmid is readily determined by assessing the quantity of fluorescence exhibited by the cells. The transfection activity of the liposomal preparations encapsulating pEGFP-C1 plasmid DNA was tested as follows. Transfection solutions were prepared by dilution of appropriate liposome or DNA samples into the desired buffer or medium. The plates were aspirated to remove medium.

Transfection solutions (0.1 ml per well for 96-well plates) were prepared by dilution of dialyzed samples containing the pEGFP-C1 plasmid into medium or buffer (approximately 2 mM total lipid unless indicated otherwise) containing 10% heat inactivated fetal bovine serum (unless otherwise designated), and were then added to the wells and incubated at 37 degrees C. for 3 hours. The wells were aspirated, and medium containing 10% heat inactivated fetal bovine serum was added to each well. Because of the previously demonstrated silencing of transgenes under the CMV promoter (Tang et al., 1997; Dion et al., 1997) a histone deacetylase inhibitor, 5 mM sodium butyrate, included in the medium to enhance expression.

After incubation at 37 degrees C. in a cell culture incubator for 18–22 hours, the medium was aspirated and a 0.5 ml wash of Dulbecco's PBS was added. At this point or just before the wash, photomicrographs were taken of the samples still on tissue culture plates with an Olympus IMT-2 inverted microscope using the 10× objective. The samples were then dissolved in detergent and readings were taken for corrected total EGFP fluorescence, in terms of the total number of live cells, using the calcein blue AM assay described above.

f. Beta Galactosidase Assay

Cells are assayed for β-galactosidase activity using the chemiluminescent β-galactosidase detection kit from Clontech according to the manufacturer's directions. Briefly, 200 µl washed IP cells are spun at 1200 rpm for two minutes. The supernatant is removed and the cell pellet lysed in 300 µl lysis buffer (100 mM potassium phosphate, pH 7.8 with 0.2% Triton X-100, prepared as described by Clontech) by vortexing for ~30 seconds and shaking gently for 15 min. Cell debris is then removed by centrifugation at 14000 rpm for 2 min. 200 µl reaction buffer is added to 45 µl cell lysate in 96 well plates, mixed and incubated for 60 min at room temperature. Luminescence is read on a microplate luminometer (EG&G Berthold), recording light signals at 5 second intregrals.

g. Sources of Materials

N-(lissamine rhodamine B sulfonyl)-phosphatidylethanolamine (transesterified from egg PC), DOPC, EPC and N—C12-DOPE were purchased from Avanti Polar Lipids (Alabaster, Ala.). OVCAR3 ovarian carcinoma cells were purchased from NCI-Frederick Cancer Research Laboratory (Frederick, Md.). The pEGFP-C1 plasmid, and *E. coli* DH5α competent cells were purchased from Clontech Laboratories (Palo Alto, Calif.). pZeoSVLacZ plasmid, competent cells and Hanahan's S.O.C. were purchased from Invitrogen (San Diego, Calif.). Hanks Balanced Salt Solution (HBSS), RPMI 1640 and heat inactivated fetal bovine serum were purchased from Gibco/BRL (Grand Island, N.Y.). DNase-free RNase and RNase-free DNase I were purchased from Boehringer Mannheim (GmbH, Germany). Agarose was purchased from FMC Bioproducts (Rockland, Me.). Bacto agar, Bacto tryptone and yeast extract were purchased from DIFCO Laboratories (Detroit, Mich.). Calcein blue acetoxy methyl ester (CBAM), PicoGreen and SybrGreen I dyes were from Molecular Probes (Eugene, Oreg.). A polylysine-transferrin (pKT) and free polylysines were obtained from Sigma (St. Louis, Mo.). pKT consists of a 30–70 kDa poly-L-lysine coupled to human holotransferrin such that there are approximately 3 transferrin molecules per polylysine. There is also an fluorescein isothiocyanate (FITC) group on each conjugate.

EXAMPLE 4

Charge Reversal Liposomes: Electrostatic Linking of Targeting/Protecting Modules to Charge Reversal Liposomes is pH-Dependent.

In one embodiment of the modular delivery inventiorr, liposomes were designed to reverse charge on a change from pH 7 to a lower pH found in cell organelles such as endosomes. To determine whether the targeting/protecting conjugates would stably bind to liposomes under conditions of physiological pH and be released from such liposomes under conditions such as lower pH, the following experiment was carried out. Liposome were made by first mixing POPE:DOPC:DODAP:Cholesterol:Cholesteryl hemisuccinate:Oleoyl acteate (51:12.2:10.7:10.7:2.6:12.8:10.7) in chloroform. EGFP plasmid, condensed with spermine, was encapsulated during liposome preparation according to the two-step emulsion method (example 1). 300 mM sucrose was used as plasmid and spermine dilution buffer. 300 mM sucrose was used in the initial hydration buffer to facilitate separation of the liposomes from bulk buffer by centrifugation. The final liposome preparation was dialyzed against PBS before use. The final lipid concentration was ~20 mM.

Cell-targeting protein complexes were bound to the external surface of the plasmid-containing liposomes through non-covalent interactions. At pH 7.4, the liposomes have a net negative charge that provides a binding surface for positively charged proteins or moieties linked to positively charged polypeptides (pKT, pK-OVB3-Ab). The number of liposomes in a 200 µl aliquot was estimated assuming a 20 mM total lipid concentration and a liposome diameter of 150 nm. Ratios of 1–5 protein complexes per liposome were tested. Protein stock solutions (FITC-labeled pKT, pK-OVB3) were made at a concentration of 0.5 mg/ml in PBS, pH 7.4. An aliquot containing the desired amount of protein was then diluted in 200 µl PBS. For a standard protein binding assay, the protein solution was added dropwise to the liposome solution with continual mixing. Equal volumes of protein solution were mixed with the liposomes at mole ratios such that the overall charge of the liposome-protein assembly remained negative. The protein/liposome mixture was incubated at room temp for 15–30 min. and then separated into two equal volume aliquots. The pH of one aliquot was lowered to pH 5 by addition of HCl, followed by incubation at room temp for an additional 15 min. Liposomes and bound protein were separated from free protein by centrifugation at 14,000 g for 30 min. The liposome pellets were resuspended in PBS and the pH of all supernatants returned to pH 7.4 with addition of NaOH before analysis. Protein levels in the supernatant were measured using the Biorad Coomassie protein assay for pK-OBV3-Ab. For the FITC-labeled pKT, fluorescence was measure for each fraction (Ex:485 Em:530). Liposomes without added ligand and protein solutions without added liposomes were used as controls.

Table 1 shows the results of the pH-dependent binding of pKT at two concentrations, 2 or 5 pKT complexes per liposome. (Note: half neutralization of the liposomal negative charge would occur with ~3 pKT bound.) At pH 7.4 virtually all of the protein pelleted with the liposome fraction during centrifugation at both pKT concentrations. When the pH was lowered to 5, a difference was found between the samples. At a pKT/liposome mole ratio of 2, all of the pKT remained associated with the liposome even at low pH. At the higher pKT/liposome ratio, a fraction of the pKT completely dissociated from the liposome at pH 5 and remained in the supernatant after centrifugation. These results suggest that there may be two types of binding sites for pKT on the liposome: A higher affinity site that is not pH-dependent and binds up to two ligand complexes per liposome and a lower affinity site where the protein complex can be toggled on or off the liposome surface by a change in pH.

Most of the pKT (~80%) remains bound to these liposomes in 20% serum, and a significant amount remains bound up to 40% serum. This amount of targeting ligand is sufficient to provide specific cell binding through a transferrin receptor.

Table 1 also shows the pH-Dependent binding of 3K-polylysine conjugated to an antibody to the OVB3 antigen, which is found on ovarian cancer cells (pK-OVB3). Analogous to the pKT study, 2 or 5 pK-OVB3-Ab complexes were bound through electrostatic interactions per negatively charged liposome. The liposomes and bound targeting ligand were separated from unbound soluble protein by centrifugation. The amount of unbound pK-OVB3-Ab in the supernatants increased significantly when the pH was lowered from 7.4 to 5 (~30% increase at a pK-OVB3-Ab/liposome mol ratio of 2, and ~50% increase at a mol ratio of 5).

Taken together, these results demonstrate that these liposomes bind a variety of targeting ligands via a cationic linker at neutral pH. At low pH, the affinity of the ligand complex may vary with the polyvalency of the cation, and at least some of the targeting complex should dissociate from the liposome at low pH. At pH 5, as in the endosomal or lysosomal compartment, the charge on cholesterol hemisuccinate should change from negative to neutral, and DODAP would become fully positively charged, resulting in a net positively charged membrane surface. This surface would have less affinity for the positively charged polylysine.

TABLE 1 pH-dependent binding of targeting modules to charge-reversal liposomes
% of total protein added found free in bulk buffer[a]

| Ligand mol ligand per mol liposomes | polylysine-transferrin[b] pH 7.4 | polylysine-transferrin[b] pH 5 | polylysine-OVB3-IgG[c] pH 7.4 | polylysine-OVB3-IgG[c] pH 5 |
|---|---|---|---|---|
| 2 | 1.5 | 0 | 0 | 30 |
| 5 | 1 | 18 | 7 | 33 |

[a]Free and liposome-associated ligand complexes separated by centrifugation.
[b]Fluorescence of FITC-labeled ligand measured for isolated liposome pellets and supernatants.
[c]Protein level measured in isolated supernatants.
[d]HCl added to sample at 7.4 to reduce the pH

EXAMPLE 5

Charge Reversal Liposomes: Binding of Serum Proteins is Minimal

Effect of Ligand Complexes on C3 Acitvation by Liposomes:

There are many factors that influence the circulation lifetime of liposomes in vivo. One critical aspect is the binding/activation of complement factor C3 by the liposomes (see Semple, et al. (1998) Advanced Drug Delivery Reviews 32:3–17 and Devine and Bradley (1998) Advanced Drug Delivery Reviews 32:19–29 for reviews); activation of C3 increased greatly liposome clearance from blood. The effect of modular targeting complexes on the activation of C3 by liposomes was tested using the pH-sensitive formulation.

Binding of C3Complement Component to Liposomes:

The ability of the liposomes to bind the C3 component of complement was tested by a modification of the in vitro hemolysis assay of Devine et al. (1994) Biochim. Biophys. Acta 1191:43–51 and Ahl et al. (1997) Biochim. Biophys. Acta 1329:370–382. Briefly, antibody-sensitized sheep erythrocytes (all reagents were from Sigma Chemical Co., St. Louis, Mo., unless noted) were washed and resuspended as directed by the manufacturer. Rat sera complement was hydrated in water then diluted 2-fold with $GVB^{2+}$ buffer. 200 μl liposomes, with or without bound targeting ligand (polylysine-transferrin, polylysine-anti-OVB3-IgG or polylysine-PEG-folate) were mixed with 100 ml diluted rat sera and incubated at 37° C. for 30 min with continuous shaking. 300 μl $GVB^{2+}$ buffer was added and any liposome aggregates pelleted by centrifugation. Eight successive 2-fold dilutions, into $GVB^{2+}$ buffer, were then done for each sample. 100 μl of the sheep erythrocytes were added to an equal volume of each liposome/sera dilution and incubated for 30 min at 37° C. with shaking. Further hemolysis was stopped by adding GVB-EDTA buffer. Intact red cells and membrane fragments were then pelleted, and the absorbance of the supernatant was measured at 415 nm. $GVB^{2+}$ buffer served as a negative control for C3 binding, and the absorbance of an equal volume of osmotically lysed red cells taken to be 100% hemolysis.

C3-mediated hemolysis curves were generated for the charge reversal liposomes with and without bound targeting ligand. The charge reversal liposomes alone gave a hemolysis profile very similar to the buffer control, suggesting little or no activation of C3 by these liposomes. When targeting complex was added, the hemolysis profile was similar to the liposome-only curve for all three targeting modules tested. The decrease in CH50 relative to buffer was determined from linear fits of the middle portion of the hemolysis curves by the method described by Ahl et al. These results are shown in Table 2. Very minor decreases (3.3–7%) in CH50 values were found for the pH-sensitive liposomes with and without bound targeting ligand. These values are significantly less than those observed by Ahl, et al. (1997) for liposomes that were rapidly cleared from the circulation of rats. They are also less than values found by those investigators for liposomes not cleared completely from the circulation in the first hour.

These results suggest that the presence of bound targeting molecules does not significantly increase the amount of liposome-mediated C3 activation. This lack of C3 activation may result in increased circulation time for these liposome vectors.

TABLE 2

Effect of targeting ligand on complement fixation by pH-sensitive liposomes

| Targeting ligand | % decrease in CH50[a] |
|---|---|
| no ligand | 3.7 ± 1.2 (3) |
| polylysine-transferrin[b] | 3.3 ± 1.7 (4) |
| polylysine-antiOVB3[c] | 4.5 ± 1.3 (4) |
| polylysine-PEG-folate[d] | 7 (1) |

[a]% decrease relative to buffer (100% CH50, 0% decrease) calculated as described by Ahl et al. The number of experiments is listed in parentheses.
[b]combined data for samples with 2–5 mol pK-transferrin per mol liposomes
[c]combined data for samples with 2–5 mol pK-anti-OBV3 per mol liposomes
[d]single sample with 5 mol pK-PEG-folate per mol liposome

EXAMPLE 6

Charge Reversal Liposomes: Enhancement of Transfection Efficiency by Targeting

NIH Ovcar-3 cells were grown as in Example 3 for ~24 h before transfection assays were performed. Aliquots of pH-sensitive liposomes containing pEGFP-C1 plasmid were mixed with a desired amount of targeting ligand in PBS and incubated at room temperature for 15 min. The sample was diluted 5-fold into RPMI with or without heat inactivated FBS and 51 μl of a 50 mM $CaCl_2$/20 mM $MgCl_2$ solution added per 0.5 ml liposomes and mixed. 90 μl liposome solution was added to PBS-washed cells in each well and incubated for ~5 h at 37° C. The transfection solution was removed, the cells washed with PBS, then allowed to incubate for 24–36 h in RPMI supplemented with 10% heat inactivated FBS and 5 mM sodium butyrate.

EGFP transgene expression was determined qualitatively by viewing the cells still in the culture plate by epifluorescence microscopy and quantitatively by reading the fluorescence intensity of each well after lysing the cells in 1% C12E8 detergent using a PE Biosystems cytofluor-4000 platereader (Ex:485 Em:530) as in Example 3. Cell viability was measured by an enzymatic fluorescent assay. Prior to lysis, the cells were incubated for 40 min in 25 μM calcein blue AM (Molecular Probes). Fluorescence intensities of the calcein blue hydrolysis product (Ex:360, Em:460) were measured during the same run as the EGFP readings. For comparison between conditions, transgene expression was corrected for cell number by dividing the EGFP reading by the calcein blue reading for each well.

The ability of the pH-triggerable liposomes to transfect cells was tested in Ovcar3 cells in vitro. Three targeting ligands were tested (pKT, pK-OVB3 and FPK) at 1, 3 or 5 protein complexes per liposome. The liposome formulation, alone or in combination with the targeting ligands, showed a small amount of cell toxicity. Calcein blue levels were approximately 20% lower for wells incubated with the plasmid-containing liposomes than for untreated cells or cells incubated overnight in media with sodium butyrate but without liposomes. The amount or type of targeting moiety did not significantly alter the level of calcein blue measured.

Transgene expression was first assessed qualitatively by epifluorescence microscopy. FIG. 1 shows representative photomicrographs of Ovcar3 cells transfected with the pH-sensitive charge reversal liposomes with pEGFP-C1 plasmid encapsulated. Without bound targeting ligand, low, but clearly visible cells filled with EGFP were observed (FIG.

Figure 1B:
Figure 8A:
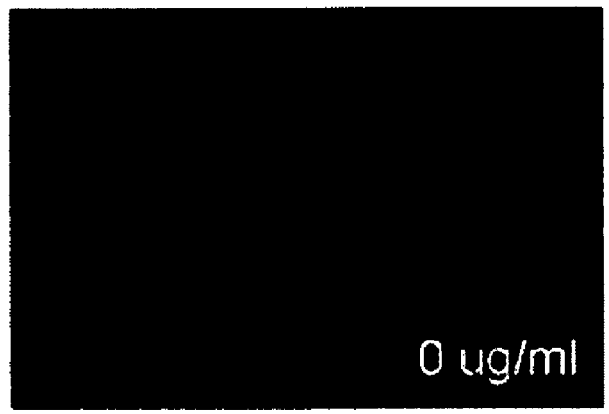
FIG. 8 depicts enhanced green fluorescent protein expression as a result of antibody targeting.
Figure 8B:
Figure 8C:
Figure 8D:
Figure 8E:
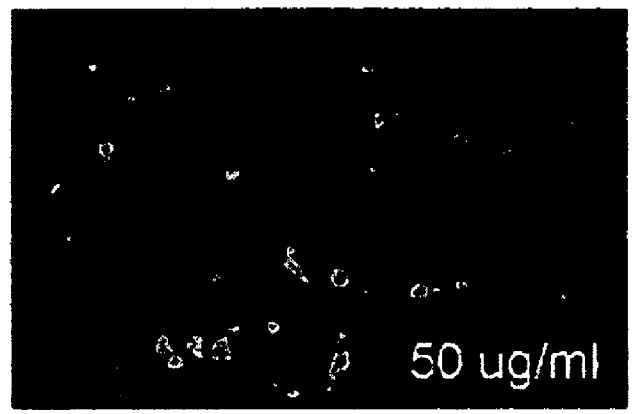
Figure 8F:
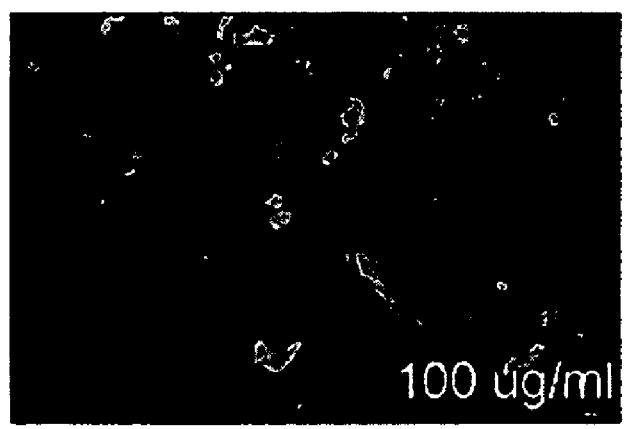
Figure 11A:
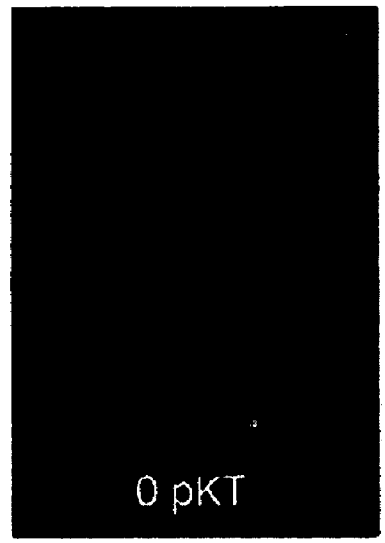
FIG. 11 is a fluorescent photomicrograph depicting the effect of pKT on liposome binding to cells and transfection.
Figure 11B:
Figure 11C:
Figure 11D:
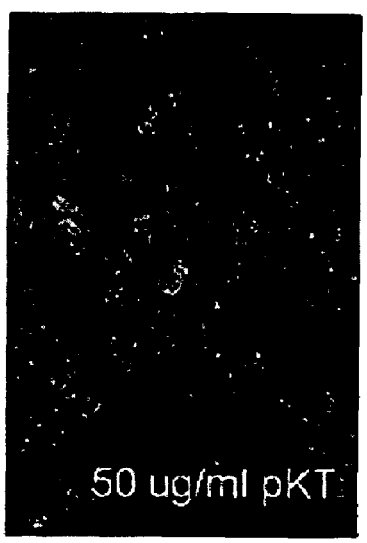
Figure 11E:

1a). With the addition of pKT, the number of cells showing green fluorescence increased (FIG. 1b). The absolute number of cells transfected varied somewhat from one transfection experiment to another. However, the relative amount of transfection, when comparing different targeting moieties, was consistent between experiments. Similar results were obtained with pK-OVB3 and FPK ligands.

The effects of increasing amounts of cell targeting moiety were determined quantitatively for pKT or FPK ligands. The results are shown in FIG. 2. The amount of transgene expression was corrected for cell number by dividing the EGFP fluorescence reading by the calcein blue reading for each well after background subtraction. This value was then multiplied by 1000 for plotting. An increase in transgene expression was found with increasing ligand concentration for all three binding targeting agents. The higher transgene expression for the pKT series, may simply reflect the increased number of targeting ligands per protein complex. pKT has 3 transferrins per polylysine chain where polylysine-PEG-folate has 1 ligand per polylysine chain. The titration of targeting complex was stopped at a 5:1 protein:liposome mol ratio to keep the overall charge of the liposomes with pKT and pK-folate negative at pH 7.4. As a control, pure 30K polylysine was used as targeting ligand at a 3:1 protein:liposome ratio. The amount of transfection was similar to that for no ligand.

EXAMPLE 7

Fusogenic N-acyl-PE Liposomes: Demonstration of Enhancement of Transfection Efficiency Mediated by Folate Targeting.

Fusogenic N-acyl-PE liposomes are negatively charged at neutral pH as are the charge neutralization liposomes. The charge density of the N-acyl-PE liposomes decreases at lower pH, but does not completely reverse. However, partial neutralization can also allow some loosening or exchange of electrostatically bound conjugates at low pH. Results and further discussion are provided in Example 8.

Liposomes composed of 70% NC12DOPE and 30% DOPC encapsulating spermine and the pEGFP-C1 plasmid were prepared as in example using the two step emulsion method followed by pelleting and washing of the liposomes to remove external DNA. A stock of liposomes 20 mM in total lipid concentration was mixed with the appropriate amount of a 340 µM stock of folate-PEG-glutaryl-protamine (FPGPr) conjugate or a control derivative in which the folate group was replaced by an acetyl group (AcPGPr). The mixture was diluted with Hanks buffered salt solution (HBSS) without $Ca^{2+}$ or $Mg^{2+}$ to reach a total lipid concentration of 4 mM and heat inactivated fetal bovine serum was added to a final concentration of 10% (v/v). To adjust the $Ca^{2+}$ and $Mg^{2+}$ concentrations to near the expected physiological levels a stock of 60 mM $CaCl_2$ and 40 mM $MgCl_2$ was added at 20 µl per ml of liposome solution just before placing the liposomes into the empty wells of the 96-well tissue culture plates. Plates were prepared and transfection analysis carried out as in Example 3.

The data are shown in FIG. 3. The folate conjugates greatly enhanced transfection efficiency of the liposomes, while a control conjugate bearing only an acetyl group did not. These data demonstrate that transfection by these liposomes is enhanced by electrostatically bound targeting/stabilizing conjugates and that the effect is dependent on the presence of folate in the conjugate. This suggests that a folate receptor is utilized.

EXAMPLE 8

Fusogenic N-acyl-PE Liposomes with Folate Targeting: Electrostatically Bound Targeting/Stabilizing Modules Versus Covalent Coupling to Lipids.

Liposomes as described in Example 7 were prepared for association with several conjugates containing folate, PEG and a positively charged group for interaction with the membrane. These conjugates were folate-PEG-protamine with a glutaryl linker (FPGPr), folate-PEG-polylysine with a glutaryl linker (FPGK) and folate-PEG-polylysine (FPK) synthesized as described in the Assays and Methods section. A folate-PEG-phosphatidylethanolamine (FPPE) derivative was also synthesized for comparison to the conjugates that interact by electrostatic interaction. The FPPE derivative inserts into the liposomal membrane and is held there by strong hydrophobic interactions. The other derivatives bind to the liposomes via an electrostatic interaction and can potentially dissociate in the endosome so that the fusogenic membrane can be exposed. The FPPE cannot dissociate as easily. The dissociation is important to remove the large PEG-containing targeting moiety for membrane fusion to occur.

Liposomes were prepared as described in Example 3, containing 200 mM sucrose with spermine and DNA. After pelleting and washing to remove external DNA, the various conjugates were associated with the liposomes. For the FPPE-containing liposomes, FPPE was incorporated into the liposomes at 2.5 mole % of the total phospholipid. The FPGK, FPK and FPGPr conjugates was added to the external leaflet of the liposomes at a concentration that also was 2.5 mole % of the external phospholipid. Buffer, serum and divalent cations were added to the samples as described in example 7 before addition to OVCAR-3 cells in 96-well plates. The final total lipid concentration was 4 mM. After incubations as described Example 7, the green fluorescence due to the expression of EGFP was determined as described in Example 3.

FIG. 4 shows the comparison between the various conjugates in that the electrostatically-linked conjugates were much more active than the covalently-linked FPPE conjugate. Similar results were obtained in which three separate preparations of the FPPE-containing liposomes were compared to the FPGPr conjugate. The FPGPr conjugate was also compared to the FPPE conjugate at a lower mole percentage in the membrane (0.4 mole %). In this case a similar result was obtained, i.e. that the FPPE conjugate showed no transfection activity, while the electrostatic conjugate showed substantial activity. The FPPE conjugate was not entirely inactive as it did show some enhancement of transfection activity with the charge reversal liposomal system (examples 4–6) at a very low mole percentage (less than 0.1 mole %).

EXAMPLE 9

Fusogenic N-acyl-PE Liposomes: Targeting Via the pK-OVB-3 Antibody Conjugate

Another embodiment of the modular targeting/stabilizing concept involves an antibody to ovarian cancer cells called OVB-3 coupled to linkers as in Example 2.

The pK-OVB-3 conjugate was found to bind to anionic liposomes, but not to zwitterionic liposomes, indicating the electrostatic nature of binding. This was demonstrated with more than one type of anionic liposome (data not shown).

Stability of Liposomal Membrane

The effect of pK-OVB-3 targeting module binding on liposome integrity was examined by fluorescent NBD-phospholipids. NBD labeled phosphatidylethanolamine (headgroup label, transesterified from egg PC) was obtained from Avanti Polar Lipids (Alabaster, Ala.) and incorporated into N-acyl-PE liposomes (example 1) at 0.5 mole % of total lipid. The membrane impermeant ion dithionite has been shown to rapidly reduce the NBD-phospholipid in the outer lipid monolayer to a non-fluorescent form. The remaining NBD-phospholipid in a sealed liposome can only be reduced following the addition of a detergent. The addition of 20 mM sodium dithionite to NBD-phospholipid labeled N—C12-DOPE/DOPC (7:3) liposomes containing encapsulated DNA (prepared as in example 1) rapidly decreased the level of NBD fluorescence from the outer monolayer as shown in FIG. 5. An approximate reduction of 50% indicates that a single bilayer membrane is found in most of the liposomes. Addition of detergent reduced the remaining NBD-phospholipid on the inner monolayer of the liposomes by dissolving the liposomes. pK-OVB3 conjugate binding to these liposomes had no significant effect on the magnitude or time course of the NBD-phospholipid reduction by sodium dithionite. This indicates that conjugate binding to the liposome surface did not significantly destabilize or alter the basic structure of these fusogenic liposomes.

Enhanced Uptake of Liposomes by pK-OVB-3:

Liposomes with pK-OVB-3 targeting modules were prepared by incubating negatively-charged liposomes with the pK-OVB-3 conjugate for 15 minutes at room temperature. During this incubation essentially all the pK-OVB-3 targeting modules are electrostatically bound to the surface of the anionic liposomes. Liposomes with pK-OVB-3 targeting modules were prepared at conjugate to lipid ratios ranging from 0 to 100 µg protein per µmole lipid. These pK-OVB-3 coated liposomes were then immediately incubated with OVCAR-3 cells at a lipid concentration of 1 mM for 1½ hours at 37° C. in the presence of 10% heat inactivated fetal calf serum. The OVCAR-3 cells were grown in Costar 96 well plates for approximately 24 hours starting at a cell concentration of 2×10⁴ cells per well. Following this incubation the OVCAR-3 cells were extensively washed by aspiration to remove unassociated liposomes. The liposomes were labeled with 0.2 mole percent of the fluorescent lipid rhodamine-DOPE to follow the liposome uptake in a fluorescent plate reader (560±10 nm excitation, 520±20 nm emission). FIG. 6 shows that increasing the amount of pK-OVB-3 targeting module bound to the surface of N—C12-DOPE/DOPC (7:3 mole ratio) liposomes significantly increase the level of OVCAR-3 cell uptake of these liposomes in the presence of 10% serum.

Enhancement of Transfection by OVB-3 Targeting:

A series of transfection experiments were performed to test the effect of the antibody conjugates. The pK-OVB-3 conjugates were prepared as described above. A stock of polylysine-OVB-3 antibody conjugate (conc. 0.5 mg/ml), a conjugate of a 3K polylysine to the OVB-3 antibody, was prepared as described above.

N—C12-DOPE/DOPC (70/30) liposomes were prepared to encapsulate the plasmid pEGFP-C1, spermine and sucrose as described in Example 1 and pelleted and washed as described in Example 1. OVCAR-3 cells were grown in 96 well plates as described in Example 3.

All transfection experiments were with OVCAR-3 cells in tissue culture, as described above. Varying amounts of the OVB-3 conjugate were added directly to a 40 mM liposome stock and diluted into HBSS without calcium or magnesium. The final total lipid concentration was 4 mM for all samples. 10% heat inactivated fetal bovine serum was added to each sample. 20 µl of a 60/40 mM Ca/Mg stock was added to every ml of liposome solution just before addition to tissue culture plates. Experiments were performed in quadruplicate.

Liposomes were incubated for transfection of OVCAR-3 cells as described above. Total cell number and transfection activity were assessed by fluorescence measurements as described above.

The results are shown in FIG. 7. In FIG. 7, the fluorescence of EGFP corrected for total cell number by the calcein blue reading was plotted against the concentration of the OVB-3-polylysine conjugate. The corresponding fluorescence photomicrographs are shown in FIG. 8. As can be seen in the Figures, the antibody-polylysine conjugate greatly enhances transfection efficiency in 10% serum.

Specificity of Enhancement of Transgene Expression for the OVB-3 Antibody:

The monoclonal antibody OVB-3 had a relatively high level of binding to OVCAR-3 cells, while non-specific mouse serum IgG binding to OVCAR-3 cells was relatively insignificant. Plasmid encapsulated N—C12-DOPE/DOPC (7:3 mole ratio) liposomes were prepared with pK-OVB3 or mouse serum pK-IgG targeting modules as desceibed above. There was no significant difference in the level of polylysine incorporation for the two antibody conjugates. The conjugate to lipid ratio for both liposome preparations was 12.5 µg protein per µmole lipid. The fusogenic liposomes were then incubated with OVCAR-3 cells for 3 hours at 37° C. at 4 mM lipid in 10% heat inactivated serum. This medium was replaced by growth medium and the cells were allowed to grow overnight. GFP transgene expression was determined by GFP fluorescence (485±10 nm excitation, 530±12 nm emission) and was normalized to the total number of living cells using a calcein blue AM fluorescence assay. The targeting module made with OVCAR-3 specific monoclonal antibody OVB-3 significantly increased GFP transgene expression of N—C12-DOPE/DOPC (7:3 mole ratio) liposomes relative to control non-targeted liposomes, while the non-specific mouse IgG-pK conjugate did not produce any significant increase in transgene expression. The relative amounts of transgene expression (normalized to 100 for the OVB-3 results) were 100±21 for the OVB-3 targeted system versus 23±5 for no targeting and 20±15 for the non-specific IgG targeted liposomes. This demonstrates the target specific characteristic of the OVB3-pK targeting module.

EXAMPLE 10

Fusogenic N-acyl-PE Liposomes: Targeting Via Polylysine-Transferrin (pKT)-Enhancement of Binding to OVCAR-3 Cells Liposomes were prepared with approximately 1 mole % Lissamine rhodamine-phosphatidylethanolamine as a fluorescent membrane probe.

Liposomes prepared as described in Example 1 (70/30 NC12-DOPE/DOPC) were incubated with varying concentrations of polylysine transferrin (pKT). The pKT was made up as a 1 mg/ml solution in Hanks balanced Salt solution (HBSS) without Ca or Mg. Since aggregation of the liposomes occurred at a ratio of approximately 0.3 g conjugate (pKT)/mmole of total phospholipid (the expected range for charge neutralization at the outer liposome surface for liposomes of this composition), pKT/liposome ratios were kept below this range for the investigations.

In order to determine if the pKT conjugate affected the binding of liposomes to OVCAR-3 ovarian cancer tumor cells, cells grown in 96 well plates were incubated with liposomes with and without the pKT conjugate electrostatically bound to the liposome. A ratio of approximately 0.2 g pKT/mmol lipid was used in all samples. Cells were incubated with liposomes at 0.1 mM, 1.0 mM, 5 mM and 15 mM total lipid in the presence and absence of serum (heat-inactivated FBS at 10%) to determine the effect of serum on binding of the liposomes to the cells. The binding solutions were prepared by adding the materials in the following order: liposomes, pKT, buffer, serum where the buffer is HBSS without without $Ca^{2+}$ or $Mg^{2+}$. Just before addition of the solutions to the cells, $Ca^{2+}$ and $Mg^{2+}$ were added to adjust the overall concentrations to 1.2 and 0.8 mM respectively. At the termination of the incubation period, the wells were aspirated, rinsed to remove unbound liposomes and binding was determined by the amount of rhodamine fluorescence bound to the cells. The results are shown in FIG. 9. Liposomes having no polylysine transferrin bound to their bilayer showed limited binding to the cell surface when incubated in the presence of serum. However, when the liposomes had polylysine transferrin bound to their surface, the binding to the cells was significantly increased. In the absence of serum, the polylysine transferrin conjugate had little effect on the liposome binding to OVCAR 3 cells. The serum proteins significantly inhibit the binding to liposomes to the cells. Transferrin pK conjugate attached to the liposomes reduced or eliminated the serum induced inhibition of liposome binding to the cells.

It is clear from the results that the addition of pKT greatly enhances binding of liposomes to these cells. Further, the pKT appears to reduce or eliminate the serum inhibition of liposome binding.

EXAMPLE 11

Fusogenic N-acyl-PE liposomes: Enhancement of Binding and Transfection by Polylysine-Transferrin Targeting N—C12-DOPE/DOPC liposomes containing spermine-condensed pEGFP plasmid DNA-liposomes and labeled by 0.5 mole % lissamine rhodamine-phosphatidylethanolamine were prepared. In one experiment, sucrose-loaded liposomes were prepared by inclusion of 200 mM sucrose in the buffer with DNA and the buffer with spermine. After removal of organic solvent and formation of liposomes and dilution into 300 mM sucrose buffer, the liposomes were extruded and dialyzed into Hanks Buffered Salt Solution without $Ca^{2+}$ and $Mg^{2+}$ (HBSS). The liposomes were then pelleted, washed and resuspended at twice the normal concentration in HBSS, i.e., to a final lipid concentration of approximately 40 mM. This stock was diluted to 20 mM and was used for experiments in 96 well plates.

As described in Example 3, 96 well plates were seeded with OVCAR-3 cells at $2\times10^5$ cells/ml of medium (RPMI 1640 with 10% fetal bovine serum) two days prior to transfection experiments. Transfections were performed, as described in Example 3, by evacuating the wells and adding 100 μl/well of the desired premixed transfection solutions and incubating at 37° C. for 3 hours. At this point, the transfection solutions were removed and 100 μl/well of RPMI 1640 medium with 10% FBS and 5 mM sodium butyrate was added. After overnight incubation at 37° C., the plates were treated for fluorescent assay of transfection as described in Example 1. Plates were washed 2× with the same detergent solution and read again in the same detergent solution. All EGFP readings were corrected by dividing by the CBAM readings for total cell esterase activity.

In parallel, a set of experiments was performed using empty liposomes labeled with a lissamine rhodamine-PE derivative (ex. 560 nm, em. 620 nm),. These were the same liposomes as described in Example 1. The liposomes served as indicators of liposomal binding under various conditions and as controls, especially in the cases where pKT was used. In the latter case, the fluorescein labeling of the pKT is a potential interference in the EGFP readings for transfection, and appropriate corrections were made in some cases. In comparison to the EGFP plasmid-containing liposomes, the rhodamine labeling level was higher, and the diameter was slightly smaller for these liposomes.

All experiments, including binding experiments, were performed in the manner of a transfection experiment, i.e. a 3 hour incubation with liposomes, followed by overnight incubation with serum and butyrate-containing medium.

Comparisons were made at a single liposome concentration and in 10% FBS, while other components varied. The order of addition of materials was as listed below. The added "buffer" was HBSS without Ca/Mg in all cases. $Ca^{2+}$ and $Mg^{2+}$ were added at the end as described above. Liposome stocks were approximately 20 mM total lipid.

Results are shown in FIG. 10. FIG. 10 demonstrates that pKT enhances the binding of liposomes to cells and transfection in a dose dependent manner. In FIG. 11, photos of the same experiments also demonstrate the pKT effect, where red fluorescence indicates liposomal lipid and green fluorescence the expression of the delivered gene.

EXAMPLE 12

Fusogenic N-acyl-PE Liposomes: Inhibition of Polylysine Transferrin Mediated Transfection by an Anti-Transferrin Antibody The effect of an anti-transferrin antibody was further investigated in this example. Liposomes and assays were prepared as described in Examples 1 and 3. Comparisons were made at 1 mM total lipid, 0.2 mg/ml pkT and in 10% FBS (always heat inactivated as in all previous examples). The samples also contained either 1.4 mg/ml anti-transferrin antibody (Sigma, St. Louis) or 1.4 mg/ml nonspecific bovine IgG (Sigma, St. Louis). Materials were added in the order described in Example 7 to prepare stocks for addition to tissue culture wells. $Ca^{2+}$ and $Mg^{2+}$ were added at the end as in Example 7.

Figure 12A:
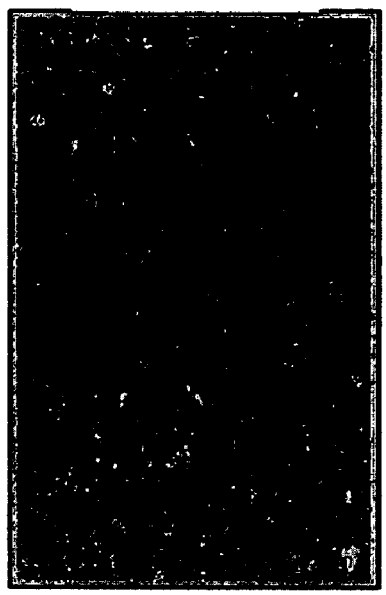
FIG. 12 demonstrates the inhibition of transfection mediated by pKT-targeted liposomes by anti-transferrin antibodies.
Figure 12B:

Photos were taken the day after the transfection incubation, and the results are shown in FIG. 12.

FIG. 12 clearly shows that the anti-transferrin inhibited transfection by the liposomes. It therefore appears that this antibody inhibits transfection mediated by the polylysine-transferrin conjugate, although binding of the liposome to cells is not strongly inhibited.

Notably, polylysine alone at a concentration approximately equal to the pKT concentration did not mediate either liposome binding or transfection (see Example 13). Therefore, it appears that the transferrin molecule plays some role in the binding of the liposomes to the cells, and undoubtedly plays a role in enhancing transfection.

EXAMPLE 13

Fusogenic N-acyl-PE Liposomes: Polylysines alone do not Mediate Liposomal Delivery and Transfection.

The OVB-3-polylysine conjugates were prepared as described above. The pK-OVB-3 was added as a 0.5 mg/ml stock to a 40 mM lipid liposome solution and then diluted with HBSS without Ca/Mg such that the final total lipid concentration was 4 mM and the pK-OVB-3 concentration of 0.1 mg/ml. The weight percent of polylysine (pK) in the conjugates was estimated to be 3%. Based on this estimate, a stock of 3 kDa pK at approximately 0.015 mg/ml was used at equal volume as the pK-OVB-3 solutions to prepare liposome conjugates, i.e. the final pK concentration was 3% of the pK-OVB-3 or 0.003 mg/ml.

The pKT sample was obtained from Sigma (St. Louis) and is described above. It contains 30–70 kDa polylysine group. For comparison to this conjugate, a 30–70 kDa polylysine (not conjugated) was obtained from Sigma (St. Louis). Based on the manufacturer's determination of approximately 0.3 polylysine (pK) units per transferrin in the conjugates, the appropriate amount of free pK was added to the liposomes in the comparison experiments. In the pKT experiments, the liposome concentration was at 2 mM total lipid and the pKT concentration 0.1 mg/ml. The liposome-pKT complexes were prepared by adding the appropriate amount of the 1 mg/ml pKT stock to a concentrated (20 mM total lipid) liposome solution and then diluting with the appropriate amount of HBSS without calcium or magnesium.

For the FPK conjugate experiments, 40 µl of a 340 µg/ml stock of FPK was added to 40 µM of 40 mM liposomes and then diluted to give a final lipid concentration of 4 mM and a final FPK concentration of 34 µg/ml.

For FPGK conjugate experiments, 80 µl of a 340 µg/ml stock of FPGK was added to 40 µl of 40 mM liposomes and then diluted to give a final lipid concentration of 4 mM and a final FPK concentration of 68 µg/ml.

The FPK and FPGK conjugates also contain 3 kDa polylysine (pK) units. For comparison of pK to the FPK and FPGK conjugates, a stock of 3 kDa pK equivalent to the FPK and FPGK solutions was used. Since the pK is approximately 40 weight % in these conjugates, a 136 µg/ml stock was used. The final lipid concentration in the transfection experiments was 4 mM and the final FPK and FPGK concentrations were 34 and 68 µg/ml respectively, while the final free pK concentration for comparison was 27 µg/ml.

N—C12-DOPE/DOPC (70/30) liposomes were prepared to encapsulate the plasmid pEGFP-C1, spermine and sucrose as described above and pelleted and washed as described above. OVCAR-3 cells were grown in 96 well plates as described above.

All transfection experiments were with OVCAR-3 cells in tissue culture, as described above. The OVB-3 conjugate were added directly to a 40 mM liposome stock and diluted into HBSS without calcium or magnesium. The final total lipid concentration was 4 mM for all samples. 10% heat inactivated fetal bovine serum was added to each sample. 20 µl of a 60/40 mM Ca/Mg stock was added to every ml of liposome solution just before addition to tissue culture plates. Experiments were performed in quadruplicate.

Liposomes were incubated for transfection of OVCAR-3 cells as described above. Total cell number and transfection activity were assessed by fluorescence measurements as described above.

The results are shown in FIG. 13. The fluorescence of EGFP corrected for total cell number by the calcein blue reading was plotted against various conditions for transfection. FIG. 13 shows that the conjugates are always much more active than the corresponding free polylysines in terms of transfection, suggesting that the activity is not mediated by the polylysine portion of the conjugates alone. The data also show that the folate conjugates enhance transfection.

EXAMPLE 14

Fusogenic N-acyl-PE Liposomes: Enhancement of Ex Vivo Binding of Liposomes to OVCAR-3 Ascites Cells by Polylysine Transferrin As the first step to testing in vivo transfection, the binding of liposomes to human OVCAR-3 ascites cells removed from a mouse xenograft was examined. Liposomes were prepared as described in Example 1. As in Example 1, both DNA-containing and empty liposomes were labeled with a rhodamine-PE fluorophore.

A series of experiments was performed using OVCAR-3 cells recovered from the ascites fluid of SCID mice. The lavage was accomplished by injection of 6 ml of PBS into the peritoneal cavity of a mouse that had been injected with $1 \times 10^7$ cells 40 days earlier. The recovered cells were pelleted and washed with PBS and resuspended at an estimated density of approximately $1–2 \times 10^6$/ml (from hemacytometer) in HBSS without Ca and Mg. Aliquots of 10, 20 or 50 µl were placed in the round-bottom wells of a polypropylene 96-well plate. HBSS was added to adjust the total volume of each well to 100 µl. At this point the plate was spun in a centrifuge, then a fine needle aspirator was used to collect the fluid. After a wash in HBSS, 50 µl of a concentrated (about 10×) cell-free intraperitoneal fluid collected from OVCAR-3-bearing SCID mice and adjusted with 20 µl/ml of a 60/40 mM $Ca^{2+}/Mg^{2+}$ stock was added to each well. Then 50 µl of each liposome sample with added $Ca^{2+}/Mg^{2+}$ was added to each well, and the wells incubated at 37° C. for 3 hours. After incubation, the wells were washed (by centrifugation) 3 times with HBSS (without Ca and Mg) and resuspended in RPMI 1640 with 10% heat inactivated fetal bovine serum and 5 mM sodium butyrate. The cells were monitored by fluorescence microscopy.

Figure 14A:
FIG. 14 demonstrates the binding of fluorescent liposomes to OVCAR-3 cells derived from the ascites of a mouse xenograft with and without a targeting agent (pKT).
Figure 14B:

The results are shown in FIG. 14. FIG. 14 reveals that pKT substantially enhanced binding of the liposomes to the OVCAR3 cells. There may have been some transfection as well. The dramatically enhanced binding seen here ex vivo would be expected to ultimately greatly enhance in vivo transfection.

EXAMPLE 15

In Vivo Transfection of Intraperitoneal OVCAR-3 Cells by Polylysine-Transferrin Targeted Liposomes In this example we treated a mouse bearing OVCAR3 tumor in a manner similar to the model presented in Son,. Cancer Gene Therapy 4, 391; 1997, incorporated herein by reference. The treatment involved injecting a very high tumor cell number into the mouse and pretreating with cisplatin before transfection.

Two high cell number OVCAR-3 SCID mice were set up as in Example 6 on day 1. On day 42, 0.2 ml of 0.5 mg/ml cisplatin was injected IP. On day 46, each mouse received an IP injection of a liposome preparation as follows: 0.5 ml of pEGFP-C1-containing liposomes (NC12-DOPE/DOPC, 70/30) were injected IP (one mouse received liposomes with the pZeoLacZ plasmid encapsulated rather than the pEGFP-C1 plasmid). The liposome stock was 40 mM total lipid, was diluted 1:1 with 1 mg/ml pKT, and was constituted in Hanks Balance Salt Solution (HBSS) without $Ca^{2+}$ or $Mg^{2+}$. Just before injection, 20 μl/ml of a stock of 60 mM and 40 mM $Ca^{+2}$ and $Mg^{2+}$, respectively, was added, which brought $Ca^{2+}$ and $Mg^{2+}$ to 1.2 and 0.8 mM respectively. The same liposome injections followed on days 49 and 52. On day 53, 0.5 ml of the same 20 mM butyrate solution in HBSS without Ca/Mg was injected IP. On day 54, both mice were sacrified and peritoneal 6 ml PBS lavage was performed on each mouse to obtain ascites cells. A fairly low number of cells was obtained, probably as a result of the platinum treatment. Some peritoneal wall and mesentery tissue was also dissected and frozen for future analysis. The ascites cells were pelleted and washed 2 times with PBS, collected into 0.5 ml and diluted 10× for observation and photographs. The pZeoLacZ-treated cells were resuspended in 5 ml of cold PBS and the pEGFP-treated cells were resuspended in 10 ml of cold PBS. A 0.3 ml aliquot of each was diuted to 1 ml in a plastic cuvette containing PBS and O.D. read at 650 nm against buffer blank. The readings were pZeoLacZ-0.836; pEGFP-0.618. A rough estimate of the pEGFP sample was that it contained 1–2e6 cells/ml. The pZeoLacZ sample was diluted by adding 1.76 ml PBS to approximate the cell concentration of the other sample. Aliquots were taken from these for chemiluminescent β-galactosidase assays, and the results are shown in FIG. 15. The EGFP sample serves as a control for the pZeoLacZ.

FIG. 15 shows that significant β-galactosidase activity occurred in the pZeoLacZ transfected cells, but only at the background level in the pEGFP control. The data confirms that in vivo transfection occurred.

EXAMPLE 16

In Vivo Transfection of OVCAR-3 Cells Under Different Conditions Mediated by Polylysine-Transferrin Targeted Liposomes Previous examples provided evidence for pKT-mediated transfection in vivo using a high cell number OVCAR-3 IP system in the SCID mice. We also utilized a lower cell number model where more mice could be treated.

11 SCID mice (female CB17 from Taconic) were injected on day 1 with $1\times10^7$ OVCAR-3 cells from tissue culture. The cells were allowed to grow until day 73. On day 73 the mice were injected intraperitoneally (IP) with 0.2 ml of 0.5 mg/ml cisplatin in PBS. On day 77, 80 and 83, the mice received IP injections of liposomes or lipid complexes. Four types of DNA-containing systems were injected (see below). On day 84, 0.5 ml of 20 mM sodium butyrate in HBSS w/o Ca/Mg was injected IP. On day 85, peritoneal lavage was performed as in Example 4. Cells from lavage samples were collected for analysis as described above. Assays for β-galactosidase were performed with a chemiluminescent substrate as in Example 3.

Group 1: Liposomes encapsulating pCMVβ plasmid (for β-galactosidase expression) at a total lipid concentration of 40 mM were mixed in equal volume with a stock of 2 mg/ml polylysine-transferrin conjugate (pKT). The liposome mixture received 12 μl per ml of a stock of 60 mM $Ca^{2+}$ and 40 mM $Mg^{2+}$ just before injection of 0.8 ml of this mixture into the peritoneal cavity of each of 4 mice.

Group 2: Exactly the same protocol except that liposomes containing the pEGFP-C1 plasmid were used.

Group 3 DC-cholesterol/DOPE (2/3) liposomes were complexed with pCMVβ plasmid DNA. A 4 mM stock of the above liposomes (prepared by sonication in a bath sonicator from a rehydrated film) in 20 mM HEPES, pH 7.0, was diluted 1:1 in distilled deionized water to give a 2 mM stock. A stock of pCMVβ plasmid DNA was diluted in water to 1 mg/ml. Equal volumes of the stocks were mixed approximately 15 minutes before intraperitoneal injection as described in examples above. 0.3 ml were injected IP into each of 2 mice.

Group 4: Exactly the same as the above DC-cholesterol complexes, except that pEGFP-C1 plasmid DNA was used. 0.3 ml was injected IP into 1 mouse.

The liposomes comprised N—C12-DOPE/DOPC (70/30) prepared sterile and as in the Assays and Methods section, including pelleting and washing. The pKT conjugate is the same as discussed above. The data are shown in FIG. 8.

Figure 16:
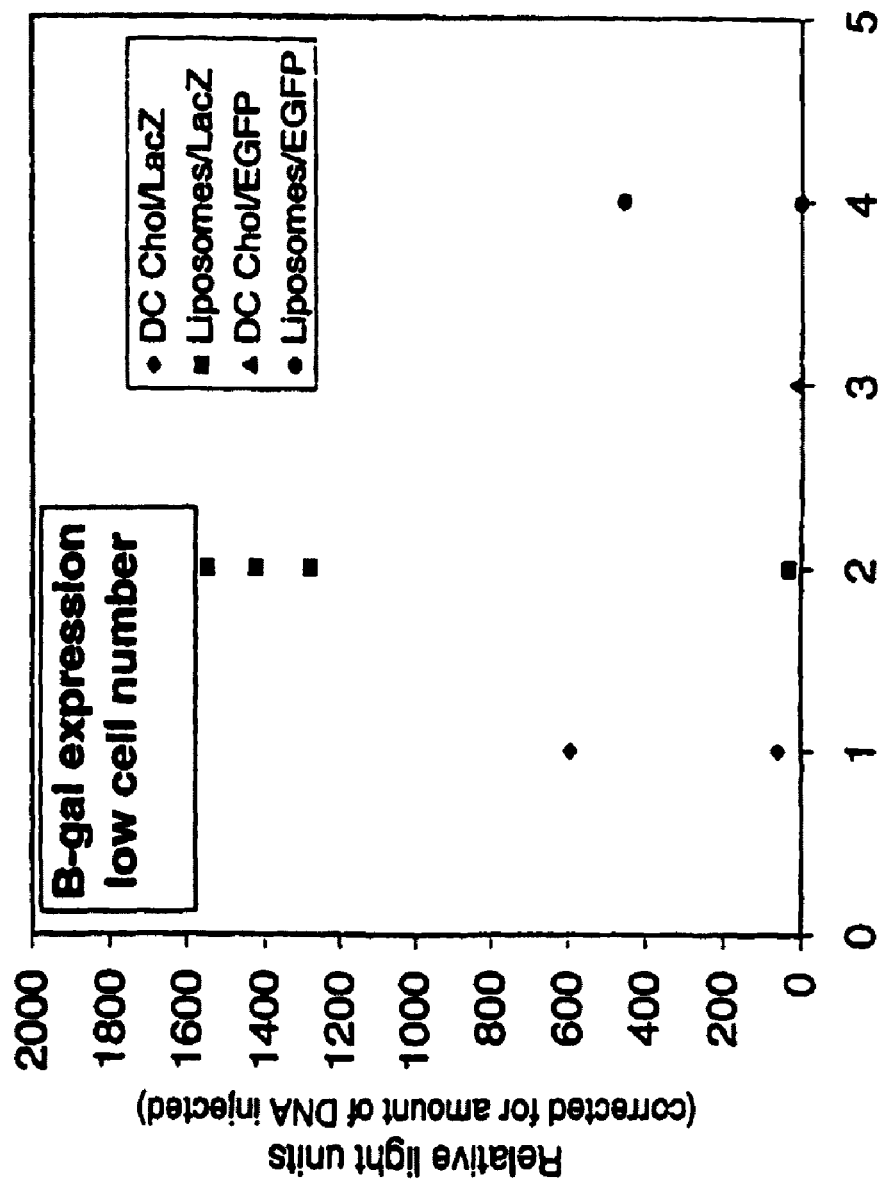
FIG. 16 demonstrates the beta-galactosidase assay for in vivo transfection.

FIG. 16 reveals that the pKT-mediated liposomal transfection of the the lacZ gene clearly worked in vivo in this IP system.

Though the invention has been described with reference to specific embodiments, those of ordinary skill in the art will recognize that various modifications, omissions, changes and/or substitutions may be made without departing from the spirit and scope of the invention defined in the appended claims.

What is claimed is:

1. A liposome comprising:
   a) a fusogenic liposome comprising a lipid bilayer encapsulating contents wherein the lipid bilayer comprises an N-acylphosphatidylethanolamine (NAPE);
   b) a releasable linking moiety electrostatically bound to said lipid bilayer of said fusogenic liposome; and
   c) a targeting moiety covalently bound to said linking moiety.

2. The liposome of claim 1, further comprising a stabilizing moiety interposed between said linking moiety and said targeting moiety, said stabilizing moiety being covalently bound to said linking moiety and said targeting moiety.

3. A liposome comprising:
   a) a fusogenic liposome comprising a lipid bilayer encapsulating contents wherein the lipid bilayer comprises an N-acylphosphatidylethanolamine (NAPE);
   b) at least one releasable linking moiety electrostatically bound to said lipid bilayer of said fusogenic liposome;
   c) a targeting moiety covalently bound to said at least one linking moiety; and
   d) a stabilizing moiety covalently bound to said at least one linking moiety.

4. The liposome of claim 1, wherein said linking moiety is at least one moiety selected from the group consisting of polylysine, protamine, polyethyleneimine, polyarginine, polyacrylate, a spermine derivative, cytochrome c, an annexin, heparin sulfate, an aminodextran, polyaspartate, polyglutamate, a polysialic acid, and poly(2-ethylacrylic acid).

5. The liposome of claim 3, wherein said at least on linking moiety is selected from the group consisting of polylysine, protamine, polyethyleneimine, polyarginine, polyacrylate, a spermine derivative, cytochrome c, an annexin, heparin sulfate, an aminodextran, polyaspartate, polyglutamate, a polysialic acid, and poly(2-ethylacrylic acid).

6. The liposome of claim 1, wherein said targeting moiety is at least one moiety selected from the group consisting of a vitamin, transferrin, an antibody, sialyl Lewis X antigen, hyaluronic acid, mannose derivatives, glucose derivatives, cell specific lectins, galaptin, galectin, lactosylceramide, a steroid derivative, an RGD sequence, EGF, EGF-binding peptide, urokiase receptor binding peptide, a thrombospondin-derived peptide, an albumin derivative and a combinatorial molecule.

7. The liposome of claim 1, wherein said contents encapsulated in said fusogenic liposome comprise at least one bioactive agent selected from the group consisting of nucleic acid, an antiviral agent, an antibacterial agent, an antifungal agent, an antimetabolic agent, an antineoplastic agent, a sterol, a carbohydrate, an amino acid, a peptides, a protein, a dye, a radio label, a radiopaque compound, a fluorescent compound, a mydriatic compound, a bronchodilator and a local anesthetic.

8. The liposome of claim 7, wherein said bioactive agent is a condensed nucleic acid.

9. The liposome of claim 2, wherein said stabilizing moiety is at least one moiety selected from the group consisting of polyethylene glycol, polyvinylpyrolidone, a dextran, a polyamino acid, methyl-polyoxazoline, polyglycerol, poly(acryloyl morpholine), and polyacrylamide.

10. A pharmaceutically composition comprising a pharmaceutically acceptable carrier and the liposome of claim 1.

* * * * *